(12) United States Patent
Barbas et al.

(10) Patent No.: US 8,586,033 B2
(45) Date of Patent: Nov. 19, 2013

(54) INTEGRIN $\alpha_{IIb}\beta_3$ SPECIFIC ANTIBODIES AND PEPTIDES

(75) Inventors: Carlos F. Barbas, Solano Beach, CA (US); Junho Chung, Pohang (KR)

(73) Assignee: The Scripps Research Institute, La Jolla, CA (US)

(*) Notice: Subject to any disclaimer, the term of this patent is extended or adjusted under 35 U.S.C. 154(b) by 1250 days.

(21) Appl. No.: 10/581,431

(22) PCT Filed: Dec. 3, 2004

(86) PCT No.: PCT/US2004/040381
§ 371 (c)(1),
(2), (4) Date: Feb. 8, 2008

(87) PCT Pub. No.: WO2005/056575
PCT Pub. Date: Jun. 23, 2005

(65) Prior Publication Data
US 2010/0297101 A1 Nov. 25, 2010

Related U.S. Application Data

(60) Provisional application No. 60/526,859, filed on Dec. 3, 2003.

(51) Int. Cl.
*A61K 39/395* (2006.01)
*C07K 16/46* (2006.01)
*C07K 16/28* (2006.01)

(52) U.S. Cl.
USPC ............. 424/130.1; 424/133.1; 424/143.1; 530/387.1; 530/387.3; 530/388.22

(58) Field of Classification Search
None
See application file for complete search history.

(56) References Cited

U.S. PATENT DOCUMENTS 5,859,205 A * 1/1999 Adair et al. ............... 530/387.3
7,812,136 B2 * 10/2010 Buettner et al. .......... 530/388.22

OTHER PUBLICATIONS

Casset et al. A peptide mimetic of an anti-CD4 monoclonal antibody by rational design. Biochem Biophys Res Commun. Jul. 18, 2003;307(1):198-205.*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol., Jul. 5, 2002,320(2):415-28.*
Eduardo Padlan, Anatomy of the antibody molecule. Mol I mmunol. Feb. 1994;31 (3): 169-217.*
Portolano et al., Lack of promiscuity in autoantigen-specific H and L chain combinations as revealed by human H and L chain "roulette". J Immunol. Feb. 1, 1993;150(3):880-7.*
Paul, Fundamental Immunology, 3rd Edition, 1993, pp. 292-295.*
Rudikoff et al. Single amino acid substitution altering antigen-binding specificity. Proc. Natl. Acad. Sci. USA, 79(6): 1979-1983, Mar. 1982.*
MacCallum et al. Antibody-antigen interactions: contact analysis and binding site topography. J Mol Biol. Oct. 11, 1996;262(5):732-45.*
Quinn et al. Quantifying GPIIb/IIIa Receptor Binding Using 2 Monoclonal Antibodies. Circulation. 1999;99:2231-2238.*
Klimka et al., Human anti-CD30 recombinant antibodies by guided phage antibody selection using cell panning. British Journal of Cancer (2000) 83:252-260.*
Beiboer et al., Guided selection of a pan carcinoma specific antibody reveals similar binding characteristics yet structural divergence between the original murine antibody and its human equivalent. J. Mol., Biol. (2000) 296:833-849.*
Biris et al. Mapping the binding domains of the alpha(IIb) subunit. A study performed on the activated form of the platelet integrin alpha(IIb)beta(3). The Federation of European Biochemical Societies Journal (Aug. 26, 2003) vol. 270, Issue: 18, pp. 3760-3767.*
Simmons et al. Shark IgNAR antibody mimotopes target a murine immunoglobulin through extended CDR3 loop structures. Proteins 2008; 71:119-130.*
Abrams et al. Determinants of specificity of a baculovirus-expressed antibody Fab fragment that binds selectively to the activated form of integrin alpha IIb beta 3. J Biol Chem. Jul. 22, 1994;269(29):18781-8.*

* cited by examiner

Primary Examiner — Maher Haddad
(74) Attorney, Agent, or Firm — Hugh Wang; Thomas Fitting; Matthew R. Kaser

(57) ABSTRACT

The present invention provides integrin $\alpha_{IIb}\beta_3$ specific antibodies and peptides. The antibodies and peptides demonstrate little or no immunoreactivity with other integrins. Methods for inhibiting platelet aggregation using the antibodies and peptides are also provided.

10 Claims, 6 Drawing Sheets

| V_H | FR1 | CDR1 | FR2 | CDR2 | FR3 | CDR3 | FR4 |
|---|---|---|---|---|---|---|---|
| | 1 | 30 31  35 | 36               49 | 50            65 | 66                                   97 | 98            113 | 114  118 |
| RAD87 | EVQLLESGGGLVQPGGSLRLSCAGSGFTFS | SYAMH | WVRQAPGKGLEWVS | AIGTGGG TYYADSVKG | RFTISRDNAKNSLYLQMNSLRAEDTAVYYCAR | VRVVCRADRRCYAMDV | WGQGT |
| RAD9  | EVQLLESGGGLVQPGGSLRLSCAGSGFTFS | SYAMH | WVRQAPGKGLEWVS | AIGTGGG TYYADSVKG | RFTISRDNAKNSLYLQMNSLRAEDTAVYYCAR | VRVVCRADRRCYAMDV | WGQGT |
| RAD12 | EVQLLESGGGLVQPGGSLRLSCAGSGFTFS | SYAMH | WVRQAPGKGLEWVS | AIGTGGG TYYADSVKG | RFTISRDNAKNSLYLQMNSLRAEDTAVYYCAR | VRVVCRADRRCYAMDV | WGQGT |
| RAD34 | EVQLLESGGGLVQPGGSLRLSCAGSGFTFS | SYAMH | WVRQAPGKGLEWVS | AIGTGGG TYYADSVKG | RFTISRDNAKNSLYLQMNSLRAEDTAVYYCAR | VRVVCRADRRCYAMDV | WGQGT |
| RAD3  | EVQLLESGGGLVHPGGSLRLSCAGSGFTFS | SYAMH | WVRQAPGKGLEWVS | AIGTGGG TYYADSVKG | RFTVSRDNSQSTAYLQINSLRAEDTAVYYCAR | VGVWCRADKRCYAMDV | WGQGT |
| RAD32 | EVQLLESGGGLVHPGGSLRLSCAGSGFTFS | SYAMH | WVRQAPGKGLEWVS | AIGTGGG TYYADSVKG | RFTVSRDNSQSTAYLQINSLRAEDTAVYYCAR | VGVWCRADKRCYAMDV | WGQGT |
| RAD88 | EVQLLESGGGLVHPGGSLRLSCAGSGFTFS | SYAMH | WVRQAPGKGLEWVS | AIGTGGG TYYADSVKG | RFTVSRDNSQSTAYLQINSLRAEDTAVYYCAR | VGVWCRADKRCYAMDV | WGQGT |
| RAD1  | EVQLLESGGGLVQPGGSLRLSCAASGFTFS | FYGMS | WVRQAPGKGLEWVS | GVSSSGITYYAASVRG | RFTISRDNSKNTLYLQMNSLRAEDTAVYYCAR | VRTHSRADRREYAMDV | WGQGT |

Figure 6

SEQUENCE LISTING

<160> NUMBER OF SEQ ID NOS: 78

<210> SEQ ID NO 1
<211> LENGTH: 11
<212> TYPE: PRT
<213> ORGANISM: Artificial Sequence
<220> FEATURE:
<223> OTHER INFORMATION: HCDR3 part

<400> SEQUENCE: 1

Cys Ser Phe Gly Arg Gly Asp Ile Arg Asn Cys
 1               5                   10

<210> SEQ ID NO 2
<211> LENGTH: 11
<212> TYPE: PRT
<213> ORGANISM: Artificial Sequence
<220> FEATURE:
<223> OTHER INFORMATION: HCDR3 part

<400> SEQUENCE: 2

Gly Ser Phe Gly Arg Gly Asp Ile Arg Asn Gly
 1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3,4,5,9,10,11)
<223> OTHER INFORMATION: encoded by randomized DNA sequence: Ala, Cys,
      Asp, Glu, Phe, Gly, His, Ile, Lys, Leu, Met, Asn, Pro, Gln, Arg,
      Ser, Thr, Val, Trp, Tyr

<400> SEQUENCE: 3

Val Gly Xaa Xaa Xaa Arg Ala Asp Xaa Xaa Xaa Tyr Ala Met Asp
 1               5                   10                  15
Val

<210> SEQ ID NO 4
<211> LENGTH: 9
<212> TYPE: PRT
<213> ORGANISM: Artificial Sequence
<220> FEATURE:
<223> OTHER INFORMATION: HCDR3 consensus part

<400> SEQUENCE: 4

Val Val Cys Arg Ala Asp Lys Arg Cys
 1               5

<210> SEQ ID NO 5
<211> LENGTH: 9
<212> TYPE: PRT
<213> ORGANISM: Artificial Sequence
<220> FEATURE:
<223> OTHER INFORMATION: HCDR3 consensus part

<400> SEQUENCE: 5

Val Trp Cys Arg Ala Asp Arg Arg Cys
 1               5

<210> SEQ ID NO 6
<211> LENGTH: 9

-continued

```
<212> TYPE: PRT
<213> ORGANISM: Artificial Sequence
<220> FEATURE:
<223> OTHER INFORMATION: HCDR3 consensus part

<400> SEQUENCE: 6

Val Trp Cys Arg Ala Asp Lys Arg Cys
 1               5

<210> SEQ ID NO 7
<211> LENGTH: 9
<212> TYPE: PRT
<213> ORGANISM: Artificial Sequence
<220> FEATURE:
<223> OTHER INFORMATION: HCDR3 consensus part

<400> SEQUENCE: 7

Val Val Cys Arg Ala Asp Arg Arg Cys
 1               5

<210> SEQ ID NO 8
<211> LENGTH: 16
<212> TYPE: PRT
<213> ORGANISM: Artificial Sequence
<220> FEATURE:
<223> OTHER INFORMATION: CDR consensus part

<400> SEQUENCE: 8

Val Arg Val Val Cys Arg Ala Asp Arg Arg Cys Tyr Ala Met Asp
 1               5                   10                  15

Val

<210> SEQ ID NO 9
<211> LENGTH: 72
<212> TYPE: DNA
<213> ORGANISM: Artificial Sequence
<220> FEATURE:
<223> OTHER INFORMATION: primer neo-rad-f
<220> FEATURE:
<221> NAME/KEY: misc_feature
<222> LOCATION: (25,26,28,29,31,32,43,44,46,47,49,50)
<223> OTHER INFORMATION: n represents a, g, c, or t

<400> SEQUENCE: 9
gtgtattact gtgcgagagt ggggnnknnk nnkcgtgccg acnnknnknn ktacgctatg      60
gacgtctggg gc                                                         72

<210> SEQ ID NO 10
<211> LENGTH: 21
<212> TYPE: DNA
<213> ORGANISM: Artificial Sequence
<220> FEATURE:
<223> OTHER INFORMATION: primer dpseq

<400> SEQUENCE: 10
agaagcgtag tccggaacgt c                                               21

<210> SEQ ID NO 11
<211> LENGTH: 57
<212> TYPE: DNA
<213> ORGANISM: Artificial Sequence
<220> FEATURE:
<223> OTHER INFORMATION: primer DP-47N-term

<400> SEQUENCE: 11
gctgcccaac cagccatggc cgaggtgcag ctgttggagt ctgggggagg cttggta        57
```

```
<210> SEQ ID NO 12
<211> LENGTH: 39
<212> TYPE: DNA
<213> ORGANISM: Artificial Sequence
<220> FEATURE:
<223> OTHER INFORMATION: primer DP-47FR3

<400> SEQUENCE: 12
cactctcgca cagtaataca cggccgtgtc ctcggctct                    39

<210> SEQ ID NO 13
<211> LENGTH: 21
<212> TYPE: DNA
<213> ORGANISM: Artificial Sequence
<220> FEATURE:
<223> OTHER INFORMATION: primer lead-VH

<400> SEQUENCE: 13
ggccatggct ggttgggcag c                                      21

<210> SEQ ID NO 14
<211> LENGTH: 39
<212> TYPE: DNA
<213> ORGANISM: Artificial Sequence
<220> FEATURE:
<223> OTHER INFORMATION: primer dp-EX

<400> SEQUENCE: 14
gaggaggagg aggaggagag aagcgtagtc cggaacgtc                   39

<210> SEQ ID NO 15
<211> LENGTH: 24
<212> TYPE: DNA
<213> ORGANISM: Artificial Sequence
<220> FEATURE:
<223> OTHER INFORMATION: primer ompseq

<400> SEQUENCE: 15
aagacagcta tcgcgattgc agtg                                   24

<210> SEQ ID NO 16
<211> LENGTH: 21
<212> TYPE: DNA
<213> ORGANISM: Artificial Sequence
<220> FEATURE:
<223> OTHER INFORMATION: primer leadB

<400> SEQUENCE: 16
ggccatggct ggttgggcag c                                      21

<210> SEQ ID NO 17
<211> LENGTH: 41
<212> TYPE: DNA
<213> ORGANISM: Artificial Sequence
<220> FEATURE:
<223> OTHER INFORMATION: primer RSC-F

<400> SEQUENCE: 17
gaggaggagg aggaggaggc ggggcccagg cggccgagct c                41

<210> SEQ ID NO 18
<211> LENGTH: 21
<212> TYPE: DNA
<213> ORGANISM: Artificial Sequence
<220> FEATURE:
<223> OTHER INFORMATION: primer lead-B
```

```
<400> SEQUENCE: 18
ggccatggct ggttgggcag c                                                    21

<210> SEQ ID NO 19
<211> LENGTH: 9
<212> TYPE: PRT
<213> ORGANISM: Homo sapiens

<400> SEQUENCE: 19

Thr His Ser Arg Ala Asp Arg Arg Glu
  1               5

<210> SEQ ID NO 20
<211> LENGTH: 9
<212> TYPE: PRT
<213> ORGANISM: Artificial Sequence
<220> FEATURE:
<223> OTHER INFORMATION: inversed RAD motif peptide

<400> SEQUENCE: 20

Val Val Cys Asp Ala Arg Arg Arg Cys
  1               5

<210> SEQ ID NO 21
<211> LENGTH: 9
<212> TYPE: PRT
<213> ORGANISM: Artificial Sequence
<220> FEATURE:
<223> OTHER INFORMATION: inversed RAD motif peptide

<400> SEQUENCE: 21

Thr His Ser Asp Ala Arg Arg Arg Glu
  1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1,2,3,7,8,9)
<223> OTHER INFORMATION: encoded by randomized DNA sequence: Ala, Cys,
      Asp, Glu, Phe, Gly, His, Ile, Lys, Leu, Met, Asn, Pro, Gln, Arg,
      Ser, Thr, Val, Trp, Tyr

<400> SEQUENCE: 22

Xaa Xaa Xaa Arg Ala Asp Xaa Xaa Xaa
  1               5

<210> SEQ ID NO 23
<211> LENGTH: 8
<212> TYPE: PRT
<213> ORGANISM: Artificial Sequence
<220> FEATURE:
<223> OTHER INFORMATION: RAD motif peptide

<400> SEQUENCE: 23

Cys Arg Ala Asp Val Pro Leu Cys
  1               5

<210> SEQ ID NO 24
<211> LENGTH: 9
<212> TYPE: PRT
<213> ORGANISM: Artificial Sequence
<220> FEATURE:
<223> OTHER INFORMATION: RAD motif peptide
```

```
<400> SEQUENCE: 24

Cys Met Ser Arg Ala Asp Arg Pro Cys
  1               5

<210> SEQ ID NO 25
<211> LENGTH: 16
<212> TYPE: PRT
<213> ORGANISM: Artificial Sequence
<220> FEATURE:
<223> OTHER INFORMATION: CDR consensus part

<400> SEQUENCE: 25

Val Arg Val Val Cys Arg Ala Asp Lys Arg Cys Tyr Ala Met Asp
  1               5                  10                  15

Val

<210> SEQ ID NO 26
<211> LENGTH: 16
<212> TYPE: PRT
<213> ORGANISM: Artificial Sequence
<220> FEATURE:
<223> OTHER INFORMATION: CDR consensus part

<400> SEQUENCE: 26

Val Arg Val Trp Cys Arg Ala Asp Arg Arg Cys Tyr Ala Met Asp
  1               5                  10                  15

Val

<210> SEQ ID NO 27
<211> LENGTH: 16
<212> TYPE: PRT
<213> ORGANISM: Artificial Sequence
<220> FEATURE:
<223> OTHER INFORMATION: CDR consensus part

<400> SEQUENCE: 27

Val Arg Val Trp Cys Arg Ala Asp Lys Arg Cys Tyr Ala Met Asp
  1               5                  10                  15

Val

<210> SEQ ID NO 28
<211> LENGTH: 16
<212> TYPE: PRT
<213> ORGANISM: Artificial Sequence
<220> FEATURE:
<223> OTHER INFORMATION: CDR consensus part

<400> SEQUENCE: 28

Val Gly Val Val Cys Arg Ala Asp Arg Arg Cys Tyr Ala Met Asp
  1               5                  10                  15

Val

<210> SEQ ID NO 29
<211> LENGTH: 16
<212> TYPE: PRT
<213> ORGANISM: Artificial Sequence
<220> FEATURE:
<223> OTHER INFORMATION: CDR consensus part

<400> SEQUENCE: 29

Val Gly Val Val Cys Arg Ala Asp Lys Arg Cys Tyr Ala Met Asp
  1               5                  10                  15

Val
```

-continued

```
<210> SEQ ID NO 30
<211> LENGTH: 16
<212> TYPE: PRT
<213> ORGANISM: Artificial Sequence
<220> FEATURE:
<223> OTHER INFORMATION: CDR consensus part

<400> SEQUENCE: 30

Val Gly Val Trp Cys Arg Ala Asp Arg Arg Cys Tyr Ala Met Asp
 1               5                  10                  15

Val

<210> SEQ ID NO 31
<211> LENGTH: 16
<212> TYPE: PRT
<213> ORGANISM: Artificial Sequence
<220> FEATURE:
<223> OTHER INFORMATION: CDR consensus part

<400> SEQUENCE: 31

Val Gly Val Trp Cys Arg Ala Asp Lys Arg Cys Tyr Ala Met Asp
 1               5                  10                  15

Val

<210> SEQ ID NO 32
<211> LENGTH: 118
<212> TYPE: PRT
<213> ORGANISM: Homo sapiens
<220> FEATURE:
<223> OTHER INFORMATION: RAD87 part

<400> SEQUENCE: 32

Glu Val Gln Leu Leu Glu Ser Gly Gly Gly Leu Val Gln Pro Gly
 1               5                  10                  15

Gly Ser Leu Arg Leu Ser Cys Ala Gly Ser Gly Phe Thr Phe Ser
                20                  25                  30

Ser Tyr Ala Met His Trp Val Arg Gln Ala Pro Gly Lys Gly Leu
                35                  40                  45

Glu Trp Val Ser Ala Ile Gly Thr Gly Gly Thr Tyr Tyr Ala
                50                  55                  60

Asp Ser Val Lys Gly Arg Phe Thr Ile Ser Arg Asp Asn Ala Lys
                65                  70                  75

Asn Ser Leu Tyr Leu Gln Met Asn Ser Leu Arg Ala Glu Asp Thr
                80                  85                  90

Ala Val Tyr Tyr Cys Ala Arg Val Gly Val Val Cys Arg Ala Asp
                95                  100                 105

Arg Arg Cys Tyr Ala Met Asp Val Trp Gly Gln Gly Thr
                110                 115

<210> SEQ ID NO 33
<211> LENGTH: 118
<212> TYPE: PRT
<213> ORGANISM: Homo sapiens
<220> FEATURE:
<223> OTHER INFORMATION: RAD9 part

<400> SEQUENCE: 33

Glu Val Gln Leu Leu Glu Ser Gly Gly Gly Leu Val Gln Pro Gly
 1               5                  10                  15

Gly Ser Leu Arg Leu Ser Cys Ala Gly Ser Gly Phe Thr Phe Ser
                20                  25                  30
```

Ser Tyr Ala Met His Trp Val Arg Gln Ala Pro Gly Lys Gly Leu
                 35                  40                  45

Glu Trp Val Ser Ala Ile Gly Thr Gly Gly Thr Tyr Tyr Ala
             50                  55                  60

Asp Ser Val Lys Gly Arg Phe Thr Ile Ser Arg Asp Asn Ala Lys
         65                  70                  75

Asn Ser Leu Tyr Leu Gln Met Asn Ser Leu Arg Ala Glu Asp Thr
             80                  85                  90

Ala Val Tyr Tyr Cys Ala Arg Val Arg Val Val Cys Arg Ala Asp
             95                 100                 105

Arg Arg Cys Tyr Ala Met Asp Val Trp Gly Gln Gly Thr
            110                 115

<210> SEQ ID NO 34
<211> LENGTH: 118
<212> TYPE: PRT
<213> ORGANISM: Homo sapiens
<220> FEATURE:
<223> OTHER INFORMATION: RAD12 part

<400> SEQUENCE: 34

Glu Val Gln Leu Leu Glu Ser Gly Gly Gly Leu Val Gln Pro Gly
 1               5                  10                  15

Gly Ser Leu Arg Leu Ser Cys Ala Gly Ser Gly Phe Thr Phe Ser
             20                  25                  30

Ser Tyr Ala Met His Trp Val Arg Gln Ala Pro Gly Lys Gly Leu
                 35                  40                  45

Glu Trp Val Ser Ala Ile Gly Thr Gly Gly Thr Tyr Tyr Ala
             50                  55                  60

Asp Ser Val Lys Gly Arg Phe Thr Ile Ser Arg Asp Asn Ala Lys
         65                  70                  75

Asn Ser Leu Tyr Leu Gln Met Asn Ser Leu Arg Ala Glu Asp Thr
             80                  85                  90

Ala Val Tyr Tyr Cys Ala Arg Val Arg Val Val Cys Arg Ala Asp
             95                 100                 105

Arg Arg Cys Tyr Ala Met Asp Val Trp Gly Gln Gly Thr
            110                 115

<210> SEQ ID NO 35
<211> LENGTH: 118
<212> TYPE: PRT
<213> ORGANISM: Homo sapiens
<220> FEATURE:
<223> OTHER INFORMATION: RAD34 part

<400> SEQUENCE: 35

Glu Val Gln Leu Leu Glu Ser Gly Gly Gly Leu Val Gln Pro Gly
 1               5                  10                  15

Gly Ser Leu Arg Leu Ser Cys Ala Gly Ser Gly Phe Thr Phe Ser
             20                  25                  30

Ser Tyr Ala Met His Trp Val Arg Gln Ala Pro Gly Lys Gly Leu
                 35                  40                  45

Glu Trp Val Ser Ala Ile Gly Thr Gly Gly Thr Tyr Tyr Ala
             50                  55                  60

Asp Ser Val Lys Gly Arg Phe Thr Ile Ser Arg Asp Asn Ala Lys
         65                  70                  75

Asn Ser Leu Tyr Leu Gln Met Asn Ser Leu Arg Ala Glu Asp Thr
             80                  85                  90

```
Ala Val Tyr Tyr Cys Ala Arg Val Arg Val Cys Arg Ala Asp
                95                 100                 105

Arg Arg Cys Tyr Ala Met Asp Val Trp Gly Gln Gly Thr
            110                 115

<210> SEQ ID NO 36
<211> LENGTH: 118
<212> TYPE: PRT
<213> ORGANISM: Homo sapiens
<220> FEATURE:
<223> OTHER INFORMATION: RAD3 part

<400> SEQUENCE: 36

Glu Val Gln Leu Leu Glu Ser Gly Gly Gly Leu Val Gln Pro Gly
 1               5                  10                  15

Gly Ser Leu Arg Leu Ser Cys Ala Gly Ser Gly Phe Thr Phe Ser
                20                  25                  30

Ser Tyr Ala Met His Trp Val Arg Gln Ala Pro Gly Lys Gly Leu
            35                  40                  45

Glu Trp Val Ser Ala Ile Gly Thr Gly Gly Gly Thr Tyr Tyr Ala
        50                  55                  60

Asp Ser Val Lys Gly Arg Phe Thr Ile Ser Arg Asp Asn Ala Lys
    65                  70                  75

Asn Ser Leu Tyr Leu Gln Met Asn Ser Leu Arg Ala Glu Asp Thr
                80                  85                  90

Ala Val Tyr Tyr Cys Ala Arg Val Arg Val Cys Arg Ala Asp
                95                 100                 105

Arg Arg Cys Tyr Ala Met Asp Val Trp Gly Gln Gly Thr
            110                 115

<210> SEQ ID NO 37
<211> LENGTH: 118
<212> TYPE: PRT
<213> ORGANISM: Homo sapiens
<220> FEATURE:
<223> OTHER INFORMATION: RAD32 part

<400> SEQUENCE: 37

Glu Val Gln Leu Leu Glu Ser Gly Gly Gly Leu Val His Pro Gly
 1               5                  10                  15

Gly Ser Leu Arg Leu Ser Cys Ala Gly Ser Gly Phe Thr Phe Ser
                20                  25                  30

Ser Tyr Ala Met His Trp Val Arg Gln Ala Pro Gly Lys Gly Leu
            35                  40                  45

Glu Trp Val Ser Ala Ile Gly Thr Gly Gly Gly Thr Tyr Tyr Ala
        50                  55                  60

Asp Ser Val Lys Gly Arg Phe Thr Val Ser Arg Asp Asn Ser Gln
    65                  70                  75

Ser Thr Ala Tyr Leu Gln Ile Asn Ser Leu Arg Ala Glu Asp Thr
                80                  85                  90

Ala Val Tyr Tyr Cys Ala Arg Val Gly Val Trp Cys Arg Ala Asp
                95                 100                 105

Lys Arg Cys Tyr Ala Met Asp Val Trp Gly Gln Gly Thr
            110                 115

<210> SEQ ID NO 38
<211> LENGTH: 118
<212> TYPE: PRT
<213> ORGANISM: Homo sapiens
```

<220> FEATURE:
<223> OTHER INFORMATION: RAD88 part

<400> SEQUENCE: 38

Glu Val Gln Leu Leu Glu Ser Gly Gly Gly Leu Val His Pro Gly
1               5                   10                  15

Gly Ser Leu Arg Leu Ser Cys Ala Gly Ser Gly Phe Thr Phe Ser
                20                  25                  30

Ser Tyr Ala Met His Trp Val Arg Gln Ala Pro Gly Lys Gly Leu
            35                  40                  45

Glu Trp Val Ser Ala Ile Gly Thr Gly Gly Thr Tyr Tyr Ala
        50                  55                  60

Asp Ser Val Lys Gly Arg Phe Thr Val Ser Arg Asp Asn Ser Gln
                65                  70                  75

Ser Thr Ala Tyr Leu Gln Ile Asn Ser Leu Arg Ala Glu Asp Thr
            80                  85                  90

Ala Val Tyr Tyr Cys Ala Arg Val Arg Val Trp Cys Arg Ala Asp
            95                  100                 105

Lys Arg Cys Tyr Ala Met Asp Val Trp Gly Gln Gly Thr
                110                 115

<210> SEQ ID NO 39
<211> LENGTH: 119
<212> TYPE: PRT
<213> ORGANISM: Homo sapiens
<220> FEATURE:
<223> OTHER INFORMATION: RAD1 part

<400> SEQUENCE: 39

Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

Phe Tyr Gly Met Ser Trp Val Arg Gln Ala Pro Gly Lys Gly Leu
            35                  40                  45

Glu Trp Val Ser Gly Val Ser Ser Ser Gly Ile Thr Thr Tyr Tyr
        50                  55                  60

Ala Ala Ser Val Arg Gly Arg Phe Thr Ile Ser Arg Asp Asn Ser
                65                  70                  75

Lys Asn Thr Leu Tyr Leu Gln Met Asn Ser Leu Arg Ala Glu Asp
            80                  85                  90

Thr Ala Val Tyr Tyr Cys Ala Arg Val Arg Thr His Ser Arg Ala
            95                  100                 105

Asp Arg Arg Glu Tyr Ala Met Asp Val Trp Gly Gln Gly Thr
                110                 115

<210> SEQ ID NO 40
<211> LENGTH: 3
<212> TYPE: PRT
<213> ORGANISM: Homo sapiens
<220> FEATURE:
<223> OTHER INFORMATION: RGD motif

<400> SEQUENCE: 40

Arg Gly Asp
1

<210> SEQ ID NO 41
<211> LENGTH: 3
<212> TYPE: PRT

```
<213> ORGANISM: Artificial Sequence
<220> FEATURE:
<223> OTHER INFORMATION: RAD motif

<400> SEQUENCE: 41

Arg Ala Asp
  1

<210> SEQ ID NO 42
<211> LENGTH: 3
<212> TYPE: PRT
<213> ORGANISM: Mus musculus
<220> FEATURE:
<223> OTHER INFORMATION: RYD motif

<400> SEQUENCE: 42

Arg Tyr Asp
  1

<210> SEQ ID NO 43
<211> LENGTH: 9
<212> TYPE: PRT
<213> ORGANISM: Homo sapiens
<220> FEATURE:
<223> OTHER INFORMATION: RAD1 part

<400> SEQUENCE: 43

Thr His Ser Arg Ala Asp Arg Arg Glu
  1               5

<210> SEQ ID NO 44
<211> LENGTH: 9
<212> TYPE: PRT
<213> ORGANISM: Homo sapiens
<220> FEATURE:
<223> OTHER INFORMATION: RAD3 part

<400> SEQUENCE: 44

Val Val Cys Arg Ala Asp Arg Arg Cys
  1               5

<210> SEQ ID NO 45
<211> LENGTH: 9
<212> TYPE: PRT
<213> ORGANISM: Homo sapiens
<220> FEATURE:
<223> OTHER INFORMATION: RAD4 part

<400> SEQUENCE: 45

Val Trp Cys Arg Ala Asp Arg Arg Cys
  1               5

<210> SEQ ID NO 46
<211> LENGTH: 9
<212> TYPE: PRT
<213> ORGANISM: Homo sapiens
<220> FEATURE:
<223> OTHER INFORMATION: RAD9 part

<400> SEQUENCE: 46

Val Val Cys Arg Ala Asp Arg Arg Cys
  1               5

<210> SEQ ID NO 47
<211> LENGTH: 9
<212> TYPE: PRT
<213> ORGANISM: Homo sapiens
<220> FEATURE:
```

```
<223> OTHER INFORMATION: RAD11 part

<400> SEQUENCE: 47

Val Trp Cys Arg Ala Asp Arg Arg Cys
 1               5

<210> SEQ ID NO 48
<211> LENGTH: 9
<212> TYPE: PRT
<213> ORGANISM: Homo sapiens
<220> FEATURE:
<223> OTHER INFORMATION: RAD12 part

<400> SEQUENCE: 48

Val Val Cys Arg Ala Asp Arg Arg Cys
 1               5

<210> SEQ ID NO 49
<211> LENGTH: 9
<212> TYPE: PRT
<213> ORGANISM: Homo sapiens
<220> FEATURE:
<223> OTHER INFORMATION: RAD32 part

<400> SEQUENCE: 49

Val Trp Cys Arg Ala Asp Lys Arg Cys
 1               5

<210> SEQ ID NO 50
<211> LENGTH: 9
<212> TYPE: PRT
<213> ORGANISM: Homo sapiens
<220> FEATURE:
<223> OTHER INFORMATION: RAD34 part

<400> SEQUENCE: 50

Val Val Cys Arg Ala Asp Arg Arg Cys
 1               5

<210> SEQ ID NO 51
<211> LENGTH: 9
<212> TYPE: PRT
<213> ORGANISM: Homo sapiens
<220> FEATURE:
<223> OTHER INFORMATION: RAD87 part

<400> SEQUENCE: 51

Val Val Cys Arg Ala Asp Arg Arg Cys
 1               5

<210> SEQ ID NO 52
<211> LENGTH: 9
<212> TYPE: PRT
<213> ORGANISM: Homo sapiens
<220> FEATURE:
<223> OTHER INFORMATION: RAD88 part

<400> SEQUENCE: 52

Val Trp Cys Arg Ala Asp Lys Arg Cys
 1               5

<210> SEQ ID NO 53
<211> LENGTH: 18
<212> TYPE: PRT
<213> ORGANISM: Homo sapiens
<220> FEATURE:
<223> OTHER INFORMATION: Anti-gp120 Fab part
```

-continued

<400> SEQUENCE: 53

Val Gly Pro Tyr Ser Trp Asp Asp Ser Pro Asp Gln Asn Tyr Tyr
1               5                   10                  15

Met Asp Val

<210> SEQ ID NO 54
<211> LENGTH: 18
<212> TYPE: PRT
<213> ORGANISM: Homo sapiens
<220> FEATURE:
<223> OTHER INFORMATION: Synthetic Construct
<220> FEATURE:
<221> NAME/KEY: VARIANT
<222> LOCATION: (4,5,6,10,11,12)
<223> OTHER INFORMATION: Fab library part; Ala, Cys, Asp, Glu, Phe, Gly,
      His, Ile, Lys, Leu, Met, Asn, Pro, Gln, Arg, Ser, Thr, Val, Trp,
      Tyr

<400> SEQUENCE: 54

Val Gly Cys Xaa Xaa Xaa Arg Gly Asp Xaa Xaa Xaa Cys Tyr Tyr
1               5                   10                  15

Met Asp Val

<210> SEQ ID NO 55
<211> LENGTH: 18
<212> TYPE: PRT
<213> ORGANISM: Homo sapiens
<220> FEATURE:
<223> OTHER INFORMATION: Fab-4 part

<400> SEQUENCE: 55

Val Gly Cys Thr Gly Gln Arg Gly Asp Trp Arg Ser Cys Tyr Tyr
1               5                   10                  15

Met Asp Val

<210> SEQ ID NO 56
<211> LENGTH: 18
<212> TYPE: PRT
<213> ORGANISM: Homo sapiens
<220> FEATURE:
<223> OTHER INFORMATION: Fab-7 part

<400> SEQUENCE: 56

Val Gly Cys Thr Tyr Gly Arg Gly Asp Thr Arg Asn Cys Tyr Tyr
1               5                   10                  15

Met Asp Val

<210> SEQ ID NO 57
<211> LENGTH: 18
<212> TYPE: PRT
<213> ORGANISM: Homo sapiens
<220> FEATURE:
<223> OTHER INFORMATION: Fab-8 part

<400> SEQUENCE: 57

Val Gly Cys Pro Ile Pro Arg Gly Asp Trp Arg Glu Cys Tyr Tyr
1               5                   10                  15

Met Asp Val

<210> SEQ ID NO 58
<211> LENGTH: 18
<212> TYPE: PRT
<213> ORGANISM: Homo sapiens
<220> FEATURE:
<223> OTHER INFORMATION: Fab-9 part

```
<400> SEQUENCE: 58

Val Gly Cys Ser Phe Gly Arg Gly Asp Ile Arg Asn Cys Tyr Tyr
 1               5                  10                  15

Met Asp Val

<210> SEQ ID NO 59
<211> LENGTH: 18
<212> TYPE: PRT
<213> ORGANISM: Homo sapiens
<220> FEATURE:
<223> OTHER INFORMATION: Fab-10 part

<400> SEQUENCE: 59

Val Gly Cys Thr Trp Gly Arg Gly Asp Glu Arg Asn Cys Tyr Tyr
 1               5                  10                  15

Met Asp Val

<210> SEQ ID NO 60
<211> LENGTH: 18
<212> TYPE: PRT
<213> ORGANISM: Homo sapiens
<220> FEATURE:
<223> OTHER INFORMATION: Synthetic Construct
<220> FEATURE:
<221> NAME/KEY: VARIANT
<222> LOCATION: (7,8,9,10)
<223> OTHER INFORMATION: MTF library part; Ala, Cys, Asp, Glu, Phe, Gly,
      His, Ile, Lys, Leu, Met, Asn, Pro, Gln, Arg, Ser, Thr, Val, Trp,
      Tyr

<400> SEQUENCE: 60

Val Gly Cys Ser Phe Gly Xaa Xaa Xaa Xaa Arg Asn Cys Tyr Tyr
 1               5                  10                  15

Met Asp Val

<210> SEQ ID NO 61
<211> LENGTH: 18
<212> TYPE: PRT
<213> ORGANISM: Homo sapiens
<220> FEATURE:
<223> OTHER INFORMATION: MTF-2 part

<400> SEQUENCE: 61

Val Gly Cys Ser Phe Gly Arg Thr Asp Gln Arg Ile Cys Tyr Tyr
 1               5                  10                  15

Met Asp Val

<210> SEQ ID NO 62
<211> LENGTH: 18
<212> TYPE: PRT
<213> ORGANISM: Homo sapiens
<220> FEATURE:
<223> OTHER INFORMATION: MTF-10 part

<400> SEQUENCE: 62

Val Gly Cys Ser Phe Gly Lys Gly Asp Asn Arg Ile Cys Tyr Tyr
 1               5                  10                  15

Met Asp Val

<210> SEQ ID NO 63
<211> LENGTH: 18
<212> TYPE: PRT
<213> ORGANISM: Homo sapiens
<220> FEATURE:
```

-continued

<223> OTHER INFORMATION: MTF-32 part

<400> SEQUENCE: 63

Val Gly Cys Ser Phe Gly Arg Arg Asn Glu Arg Asn Cys Tyr Tyr
 1               5                  10                  15

Met Asp Val

<210> SEQ ID NO 64
<211> LENGTH: 18
<212> TYPE: PRT
<213> ORGANISM: Homo sapiens
<220> FEATURE:
<223> OTHER INFORMATION: MTF-40 part

<400> SEQUENCE: 64

Val Gly Cys Ser Phe Gly Arg Asn Asp Ser Arg Asn Cys Tyr Tyr
 1               5                  10                  15

Met Asp Val

<210> SEQ ID NO 65
<211> LENGTH: 18
<212> TYPE: PRT
<213> ORGANISM: Homo sapiens
<220> FEATURE:
<223> OTHER INFORMATION: MTF-1 part

<400> SEQUENCE: 65

Val Gly Cys Ser Phe Gly Arg Val Asp Arg Asn Cys Tyr Tyr
 1               5                  10                  15

Met Asp Val

<210> SEQ ID NO 66
<211> LENGTH: 18
<212> TYPE: PRT
<213> ORGANISM: Homo sapiens
<220> FEATURE:
<223> OTHER INFORMATION: MTF-12 part

<400> SEQUENCE: 66

Val Gly Cys Ser Phe Gly Arg Ala Asp Arg Arg Asn Cys Tyr Tyr
 1               5                  10                  15

Met Asp Val

<210> SEQ ID NO 67
<211> LENGTH: 18
<212> TYPE: PRT
<213> ORGANISM: Homo sapiens
<220> FEATURE:
<223> OTHER INFORMATION: MTF-15 part

<400> SEQUENCE: 67

Val Gly Cys Ser Phe Gly Arg Ser Val Asp Arg Asn Cys Tyr Tyr
 1               5                  10                  15

Met Asp Val

<210> SEQ ID NO 68
<211> LENGTH: 18
<212> TYPE: PRT
<213> ORGANISM: Homo sapiens
<220> FEATURE:
<223> OTHER INFORMATION: MTF-7 part

<400> SEQUENCE: 68

Val Gly Cys Ser Phe Gly Lys Arg Asp Met Arg Asn Cys Tyr Tyr

<210> SEQ ID NO 69
<211> LENGTH: 18
<212> TYPE: PRT
<213> ORGANISM: Homo sapiens
<220> FEATURE:
<223> OTHER INFORMATION: MTF-13 part

<400> SEQUENCE: 69

Val Gly Cys Ser Phe Gly Arg Trp Asp Ala Arg Asn Cys Tyr Tyr
 1               5                  10                  15
Met Asp Val

<210> SEQ ID NO 70
<211> LENGTH: 18
<212> TYPE: PRT
<213> ORGANISM: Homo sapiens
<220> FEATURE:
<223> OTHER INFORMATION: MTF-14 part

<400> SEQUENCE: 70

Val Gly Cys Ser Phe Gly Arg Gln Asp Val Arg Asn Cys Tyr Tyr
 1               5                  10                  15
Met Asp Val

<210> SEQ ID NO 71
<211> LENGTH: 18
<212> TYPE: PRT
<213> ORGANISM: Homo sapiens
<220> FEATURE:
<223> OTHER INFORMATION: MTF-20 part

<400> SEQUENCE: 71

Val Gly Cys Ser Phe Gly Arg Asp Asp Gly Arg Asn Cys Tyr Tyr
 1               5                  10                  15
Met Asp Val

<210> SEQ ID NO 72
<211> LENGTH: 16
<212> TYPE: PRT
<213> ORGANISM: Homo sapiens
<220> FEATURE:
<223> OTHER INFORMATION: Synthetic Construct
<220> FEATURE:
<221> NAME/KEY: VARIANT
<222> LOCATION: (3,4,5,9,10,11)
<223> OTHER INFORMATION: RAD library part; Ala, Cys, Asp, Glu, Phe, Gly,
      His, Ile, Lys, Leu, Met, Asn, Pro, Gln, Arg, Ser, Thr, Val, Trp,
      Tyr

<400> SEQUENCE: 72

Val Arg Xaa Xaa Xaa Arg Ala Asp Xaa Xaa Xaa Tyr Ala Met Asp
 1               5                  10                  15
Val

<210> SEQ ID NO 73
<211> LENGTH: 16
<212> TYPE: PRT
<213> ORGANISM: Homo sapiens
<220> FEATURE:

```
<223> OTHER INFORMATION: RAD1 part

<400> SEQUENCE: 73

Val Arg Thr His Ser Arg Ala Asp Arg Arg Gly Tyr Ala Met Asp
 1               5                  10                  15

Val

<210> SEQ ID NO 74
<211> LENGTH: 16
<212> TYPE: PRT
<213> ORGANISM: Homo sapiens
<220> FEATURE:
<223> OTHER INFORMATION: RAD3 part, RAD9 part, RAD12 part, and RAD34
      part

<400> SEQUENCE: 74

Val Arg Val Val Cys Arg Ala Asp Arg Arg Cys Tyr Ala Met Asp
 1               5                  10                  15

Val

<210> SEQ ID NO 75
<211> LENGTH: 16
<212> TYPE: PRT
<213> ORGANISM: Homo sapiens
<220> FEATURE:
<223> OTHER INFORMATION: RAD4 part and RAD11 part

<400> SEQUENCE: 75

Val Gly Val Trp Cys Arg Ala Asp Arg Arg Cys Tyr Ala Met Asp
 1               5                  10                  15

Val

<210> SEQ ID NO 76
<211> LENGTH: 16
<212> TYPE: PRT
<213> ORGANISM: Homo sapiens
<220> FEATURE:
<223> OTHER INFORMATION: RAD32 part

<400> SEQUENCE: 76

Val Gly Val Trp Cys Arg Ala Asp Lys Arg Cys Tyr Ala Met Asp
 1               5                  10                  15

Val

<210> SEQ ID NO 77
<211> LENGTH: 16
<212> TYPE: PRT
<213> ORGANISM: Homo sapiens
<220> FEATURE:
<223> OTHER INFORMATION: RAD87 part

<400> SEQUENCE: 77

Val Gly Val Val Cys Arg Ala Asp Arg Arg Cys Tyr Ala Met Asp
 1               5                  10                  15

Val

<210> SEQ ID NO 78
<211> LENGTH: 16
<212> TYPE: PRT
<213> ORGANISM: Homo sapiens
<220> FEATURE:
<223> OTHER INFORMATION: RAD88 part
```

```
<400> SEQUENCE: 78

Val Arg Val Trp Cys Arg Ala Asp Lys Arg Cys Tyr Ala Met Asp
 1               5                  10                  15
Val
```

INTEGRIN $\alpha_{IIb}\beta_3$ SPECIFIC ANTIBODIES AND PEPTIDES

RELATION TO OTHER APPLICATIONS

This is a national phase filing under 35 U.S.C. §371 of international application No. PCT/US2004/040381 filed on 3 Dec. 2004 and published on 23 Jun. 2005 as WO 2005/056575 and claims priority to and benefit of U.S. 60/526,859 filed on 3 Dec. 2003, all of which applications and publications are explicitly incorporated by reference herein.

TECHNICAL FIELD OF THE INVENTION

The field of this invention is platelet aggregation. More particularly, the present invention pertains to integrin specific antibodies and peptides and the use of those compounds for inhibiting platelet aggregation.

CD-R 1 contains the Sequence Listing formatted in plain ASCII text. The Sequence Listing is entitled TSRI 1019.1 US.TXT, created on May 31, 2006, and is 5,060 Bytes in size. CD-R 1 is labeled with Identification No. TSRI 1019.1 US, copy I.

CD-R 2 is an exact copy of CD-R 1. CD-R 2 is labeled with Identification No. TSRI 1019.1 US, Copy 2.

CD-R 3 contains the Computer Readable Form of the Sequence Listing in compliance with 37 C.F.R. §1.82I(e), and specified by 37 C.F.R. §1.824. CD-R 3 is labeled with Identification No. TSRI 1019.1 US, Copy 3.

The disclosure of the Sequence Listing submitted as an electronic document on compact disc as described above are to be part of the permanent USPTO record of this patent application and are hereby expressly incorporated by reference.

BACKGROUND OF THE INVENTION

Integrin $\alpha_{IIb}\beta_3$ inhibitors are new class of antithrombotic agents that block fibrinogen binding to the platelet integrin $\alpha_{IIb}\beta_3$, thereby inhibiting platelet-platelet interactions essential for the formation of platelet thrombi (Topol, E. J., Byzova, T. V., and Plow, E. F. (1999) Platelet GPIIb-IIIa blockers. *Lancet* 353, 227-231; Coller, B. S. (1997) Platelet GPIIb/IIIa antagonists: the first anti-integrin receptor therapeutics. *J Clin Invest* 99, 1467-1471). Integrin $\alpha_{IIb}\beta_3$ inhibitors are used for the management of patients with non-ST-segment elevation acute coronary syndromes and patients undergoing percutaneous coronary intervention (Proimos, G. (2001) Platelet aggregation inhibition with glycoprotein IIb-IIIa inhibitors. *J Thromb Thrombolysis* 11, 99-110). Among these inhibitors, abciximab (ReoPro, Centocor, Inc., Malvern, Pa., and Eli Lilly & Company, Indianapolis, Ind.) (Coller, B. S. (1997) Platelet GPIIb/IIIa antagonists: the first anti-integrin receptor therapeutics. *J Clin Invest* 99, 1467-1471), eptifibatide (INTEGRILIN, COR Therapeutics, Inc., South San Francisco, Calif., and Key Pharmaceuticals, Inc., Kenilworth, N.J.) (Phillips, D. R., and Scarborough, R. M. (1997) Clinical pharmacology of eptifibatide. *Am J Cardiol* 80, 11B-20B; Scarborough, R. M. (1999) Development of eptifibatide. *Am Heart J* 138, 1093-1104), and tirofiban (Aggrastat, Merck & Co., Inc., Whitehouse Station, N.J.) (Vickers, S., Theoharides, A. D., Arison, B., Balani, S. K., Cui, D., Duncan, C. A., Ellis, J. D., Gorham, L. M., Polsky, S. L., Prueksaritanont, T., Ramjit, H. G., Slaughter, D. E., and Vyas, K. P. (1999) In vitro and in vivo studies on the metabolism of tirofiban. *Drug Metab Dispos* 27, 1360-1366) are clinically approved in the United States. Abciximab, the first approved and most widely used agent, is a chimeric Fab with mouse variable and human constant domains. It binds to an epitope adjacent to the ligand binding region and inhibits fibrinogen binding by steric hindrance. Abciximab was reported to cross-react with integrin $\alpha_v\beta_3$ and $\alpha_M\beta_2$ (Scarborough, R. M. (1999) Development of eptifibatide. *Am Heart J* 138, 1093-1104). Eptitibatide and tirofiban, on the other hand, are small molecule drugs that bind to the RGD ligand interaction site of the integrin and are $\alpha_{IIb}\beta_3$-specific. They showed lower affinity and much shorter circulatory half-lives than abciximab (Scarborough, R. M. (1999) Development of eptifibatide. *Am Heart J* 138, 1093-1104; Vickers, S., Theoharides, A. D., Arison, B., Balani, S. K., Cui, D., Duncan, C. A., Ellis, J. D., Gorham, L. M., Polsky, S. L., Prueksaritanont, T., Ramjit, H. G., Slaughter, D. E., and Vyas, K. P. (1999) In vitro and in vivo studies on the metabolism of tirofiban. *Drug Metab Dispos* 27, 1360-1366; McClellan, K. J., and Goa, K. L. (1998) Tirofiban. A review of its use in acute coronary syndromes. *Drugs* 56, 1067-1080).

Acute thrombocytopenia is a recognized complication of treatment with integrin $\alpha_{IIb}\beta_3$ inhibitors. Thrombocytopenia, often severe (platelets less than $50 \times 10^9$/L), occurs in 0.5% to 1% of patients given abciximab for the first time (Berkowitz, S. D., Sane, D. C., Sigmon, K. N., Shavender, J. H., Harrington, R. A., Tcheng, J. E., Topol, E. J., and Califf, R. M. (1998) Occurrence and clinical significance of thrombocytopenia in a population undergoing high-risk percutaneous coronary revascularization. Evaluation of c7E3 for the Prevention of Ischemic Complications (EPIC) Study Group. *J Am Coll Cardiol* 32, 311-319; Jubelirer, S. J., Koenig, B. A., and Bates, M. C. (1999) Acute profound thrombocytopenia following C7E3 Fab (Abciximab) therapy: case reports, review of the literature and implications for therapy. *Am J Hematol* 61, 205-208; Kereiakes, D. J., Berkowitz, S. D., Lincoff, A. M., Tcheng, J. E., Wolski, K., Achenbach, R., Melsheimer, R., Anderson, K., Califf, R. M., and Topol, E. J. (2000) Clinical correlates and course of thrombocytopenia during percutaneous coronary intervention in the era of abciximab platelet glycoprotein IIb/IIIa blockade. *Am Heart J* 140, 74-80) and in 4% of patients after the second administration (Madan, M., Kereiakes, D. J., Hermiller, J. B., Rund, M. M., Tudor, G., Anderson, L., McDonald, M. B., Berkowitz, S. D., Sketch, M. H., Jr., Phillips, H. R., 3rd, and Tcheng, J. E. (2000) Efficacy of abciximab readministration in coronary intervention. *Am J Cardiol* 85, 435-440; Tcheng, J. E., Kereiakes, D. J., Braden, G. A., Jordan, R. E., Mascelli, M. A., Langrall, M. A., and Effron, M. B. (1999) Readministration of abciximab: interim report of the ReoPro readministration registry. *Am Heart J* 138, S33-38). In clinical trials of tirofiban the incidence ranged from 0.1% to 0.5%, which is only twice the incidence seen in patients not given the drug (The RESTORE Investigators. Randomized Efficacy Study of Tirofiban for Outcomes and REstenosis (1997) Effects of platelet glycoprotein IIb/IIIa blockade with tirofiban on adverse cardiac events in patients with unstable angina or acute myocardial infarction undergoing coronary angioplasty. *Circulation* 96, 1445-1453; Platelet Receptor Inhibition in Ischemic Syndrome Management (PRISM) Study Investigators. (1998) A comparison of aspirin plus tirofiban with aspirin plus heparin for unstable angina. *N Engl J Med* 338, 1498-1505; Platelet Receptor Inhibition in Ischemic Syndrome Management in Patients Limited by Unstable Signs and Symptoms (PRISM-PLUS) Study Investigators. (1998) Inhibition of the platelet glycoprotein IIb/IIIa receptor with tirofiban in unstable angina and non-Q-wave myocardial infarction. *N Engl J Med* 338, 1488-1497). In the PURSUIT trial of eptifibatide, the incidence was approximately the same in patients given the study drug as in patients given placebo (McClure, M. W, Berkowitz, S. D., Sparapani, R., Tuttle, R., Kleiman, N. S., Berdan, L. G., Lincoff, A. M., Deckers, J., Diaz, R., Karsch, K. R., Gretler, D., Kitt, M., Simoons, M., Topol, E. J., Califf, R. M., and Harrington, R. A. (1999) Clinical significance of thrombocytopenia during a non-ST-elevation acute coronary syndrome. The platelet glycoprotein IIb/IIIa in unstable angina: receptor suppression using integrilin therapy (PURSUIT) trial experience. *Circulation* 99, 2892-2900). Only a small subset of patients given eptifibatide had profound, unexplained thrombocytopenia (McClure, M. W, Berkowitz, S. D., Sparapani, R., Tuttle, R., Kleiman, N. S., Berdan, L. G., Lincoff, A. M., Deckers, J., Diaz, R., Karsch, K. R., Gretler, D., Kitt, M., Simoons, M., Topol, E. J., Califf, R. M., and Harrington, R. A. (1999) Clinical significance of thrombocytopenia during a non-ST-elevation acute coronary syndrome. The platelet glycoprotein IIb/IIIa in unstable angina: receptor suppression using integrilin therapy (PURSUIT) trial experience. *Circulation* 99, 2892-2900). The cause of thrombocytopenia induced by integrin $\alpha_{IIb}\beta_3$ inhibitors is not known, although recently it was reported that human antibodies against the mouse variable domains of abciximab, presumably induced by the first exposure of abciximab, were the cause of platelet destruction in patients who developed severe thrombocytopenia after being given abciximab a second time (Curtis, B. R., Swyers, J., Divgi, A., McFarland, J. G., and Aster, R. H. (2002) Thrombocytopenia after second exposure to abciximab is caused by antibodies that recognize abciximab-coated platelets. *Blood* 99, 2054-2059).

Integrins $\alpha_v\beta_3$, $\alpha_v\beta_5$, $\alpha_{IIb}\beta_3$, and $\alpha_5\beta_1$ bind to a variety of adhesive protein containing an Arg-Gly-Asp (RGD) tripeptide. Exploiting this feature, adhesive protein-mimicking synthetic human mAbs containing an RGD motif in HCDR3 flanked by six randomized residues were selected from antibody libraries by phage display (Barbas, C. F., 3rd, Languino, L. R., and Smith, J. W. (1993) High-affinity self-reactive human antibodies by design and selection: targeting the integrin ligand binding site. *Proc Natl Acad Sci USA* 90, 10003-10007). Fab-9, the most potent of these antibodies, binds to integrin $\alpha_v\beta_3$ nearly 1,000-fold better than to integrins $\alpha_v\beta_5$ and $\alpha_5\beta_1$. However, neither of the selected antibodies including Fab-9 distinguished between the two $\beta_3$ integrins, $\alpha_v\beta_3$ and $\alpha_{IIb}\beta_3$. Therefore, a motif optimization library was generated to determine whether further rounds of engineering and selection on the RGD motif within the HCDR3 of Fab-9 could produce an antibody with specificity for either integrin $\alpha_v\beta_3$ or $\alpha_{IIb}\beta_3$ (Smith, J. W., Hu, D., Satterthwait, A., Pinz-Sweeney, S., and Barbas, C. F., 3rd (1994) Building synthetic antibodies as adhesive ligands for integrins. *J Biol Chem* 269, 32788-32795). While many of the selected antibodies showed some preference to either integrin $\alpha_v\beta_3$ or integrin $\alpha_{IIb}\beta_3$, all antibodies still bound to both integrins. The majority of the selected antibodies had the consensus sequence (K/R)XD. Interestingly, the middle position in the RGD motif proved to be highly permissive. It was found that the Gly can be substituted by Val, Ala, Asn, Arg, Thr, Gln, Asp, Ser, and Trp (Smith, J. W., Hu, D., Satterthwait, A., Pinz-Sweeney, S., and Barbas, C. F., 3rd (1994) Building synthetic antibodies as adhesive ligands for integrins. *J Biol Chem* 269, 32788-32795).

BRIEF SUMMARY OF THE INVENTION

In one preferred embodiment the invention is an isolated and purified peptide inhibitor of platelet aggregation, the peptide comprising from 9 to about 50 amino acid residues and having an amino acid residue sequence that is selected from the group consisting of SEQ ID Nos: 4, 5, 6, and 7. In a preferred embodiment the peptide comprises the amino acid residue sequence of any of SEQ ID NOs:5-7. In another preferred embodiment, the peptide consists of any of SEQ ID NOs:5-7. In a more preferred embodiment, the peptide consists essentially of any of SEQ ID NOs:5-7.

In another embodiment the invention contemplates an antibody that specifically immunoreacts with integrin $\alpha_{IIb}\beta_3$ and comprises an amino acid residue sequence selected from the group consisting of SEQ ID Nos: 8, 25, 26, 27, 28, 29, 30, and 31, wherein the amino acid residue sequence is within a complementarity determining region (CDR) of the antibody. In a preferred embodiment, the complementarity determining region of the antibody is located in a heavy chain of the antibody. In a more preferred embodiment, the complementarity determining region of the antibody is HCDR3.

In yet another embodiment, the antibody is selected from the group consisting of the antibodies designated herein as RAD3, RAD4, RAD9, RAD11, RAD12, RAD32, RAD34, RAD87, or RAD88 and that has immunoreactivity with integrin $\alpha_{IIb}\beta_3$. In a preferred embodiment the antibody is a human antibody.

In a still further embodiment, the invention contemplates an antibody having immunoreactivity with integrin $\alpha_{IIb}\beta_3$.

The invention also contemplates methods of using the antibodies, immunoglobulins, and peptides of the invention. In one embodiment, the method is a method of inhibiting platelet aggregation comprising contacting platelets with an effective inhibitory amount of a peptide having an amino acid residue sequence that is selected from the group consisting of SEQ ID Nos: 4, 5, 6, and 7.

In an additional embodiment, the method is a method of inhibiting platelet aggregation comprising contacting platelets with an effective inhibitory amount of the antibody that specifically immunoreacts with integrin $\alpha_{IIb}\beta_3$ and comprises an amino acid residue sequence selected from the group consisting of SEQ ID Nos: 8, 25, 26, 27, 28, 29, 30, and 31, wherein the amino acid residue sequence is within a complementarity determining region of the antibody.

The invention also contemplates a method of inhibiting binding of fibrinogen to platelets comprising contacting the platelets with an effective inhibitory amount of a peptide having an amino acid residue sequence that is selected from the group consisting of SEQ ID Nos: 4, 5, 6, and 7.

The invention still further contemplates a method of inhibiting platelet aggregation comprising contacting platelets with an effective inhibitory amount of an antibody that specifically immunoreacts with integrin $\alpha_{IIb}\beta_3$ and comprises an amino acid residue sequence selected from the group consisting of SEQ ID Nos: 8, 25, 26, 27, 28, 29, 30, and 31, wherein the amino acid residue sequence is within a complementarity determining region of the antibody.

The invention still further contemplates an antibody having integrin $\alpha_{IIb}\beta_3$-binding activity, wherein the binding competes with binding activity of another protein, the other protein comprising an amino acid residue sequence of the tripeptide motif Arg-Ala-Asp (RAD) and wherein the binding is performed in a standard competition assay. In a further embodiment, the protein is another antibody, the other antibody comprising an amino acid residue sequence within a complementarity determining region of the other antibody, wherein the amino acid sequence is selected from the group consisting of SEQ ID Nos: 8, 25, 26, 27, 28, 29, 30, and 31, and wherein the binding is performed in a standard competition assay.

A further embodiment of the invention contemplates a pharmaceutical composition comprising the peptide inhibitor of platelet aggregation and a suitable pharmaceutical carrier in a form suitable for administration intravenously, intra-arterially, into the lymphatic circulation, intraperitoneally, transdermally, subcutaneously, intramuscularly, into the joint space, or by pulmonary administration. A still further embodiment contemplates a pharmaceutical composition comprising the antibody that specifically immunoreacts with integrin $\alpha_{IIb}\beta_3$ and a suitable pharmaceutical carrier.

An additional embodiment of the invention contemplates using the peptide inhibitor of platelet aggregation as a medicament for treatment to prevent thrombosis in conditions selected from the group consisting of pulmonary embolism, transient ischemic attacks (TIAs), deep vein thrombosis, coronary bypass surgery, and surgery to insert a prosthetic valve or vessel in autologous, non-autologous, or synthetic vessel graft. A further embodiment contemplates using the antibody that specifically immunoreacts with integrin $\alpha_{IIb}\beta_3$ as a medicament for treatment to prevent thrombosis.

In another embodiment the peptide inhibitor of platelet aggregation can also be used as a medicament for treatment to prevent thrombosis in procedure selected from the group consisting of angioplasty procedures performed by balloon, coronary atherectomy, and laser angioplasty. In a further embodiment the antibody that specifically immunoreacts with integrin $\alpha_{IIb}\beta_3$ is used as a medicament for treatment to prevent thrombosis.

The invention also contemplates a method of treating a subject to treat or prevent a disorder of thrombus formation, the disorder selected from the group consisting of thrombosis in pulmonary embolism, transient ischemic attacks (TIAs), deep vein thrombosis, coronary bypass surgery, surgery to insert a prosthetic valve or vessel in autologous, non-autologous, or synthetic vessel graft, the method comprising administering to the subject an amount of a peptide having activity that inhibits platelet aggregation effective to achieve the desired treatment. An additional embodiment of the invention contemplates a method of treating a subject to treat or prevent a disorder of thrombus formation comprising administering to the subject an amount of an antibody that specifically immunoreacts with integrin $\alpha_{IIb}\beta_3$ effective to achieve the desired treatment.

In one aspect, the present invention provides an isolated and purified peptide inhibitor of platelet aggregation. The peptide has from 9 to about 50 amino acid residues and an amino acid residue sequence that corresponds to V(V/W) CRAD(K/R)RC (exemplified by SEQ ID NOs:4, 5, 6, and 7). The peptide preferably includes the amino acid residue sequence of any of SEQ ID NOs: 5-7 and, more preferably, has the amino acid residue sequence of any of SEQ ID NOs: 5-7.

In another aspect, the invention provides an antibody that specifically immunoreacts with integrin $\alpha_{IIb}\beta_3$. The antibody includes the amino acid residue sequence V(R/G)V(V/W) CRAD (R/K)RCYAMDV (exemplified by SEQ ID NOs:8, 25, 26, 26, 28, 29, 30, and 31) within a complementarity determining region of the antibody. Preferably, the complementarity determining region is located in a heavy chain of the antibody and, more particularly, the complementarity determining region is HCDR3. The antibody is most preferably a human antibody. Exemplary and preferred antibodies are 5 designated herein as RAD3, RAD4, RAD9, RAD11, RAD12, RAD32, RAD34, RAD87, or RAD88. The invention also contemplates an antibody having the immunoreactivity of any of RAD3, RAD4, RAD9, RAD11, RAD12, RAD32, RAD34, RAD87, or RAD88.

In yet another aspect, this invention provides a method of inhibiting platelet aggregation including the step of contacting platelets with an effective inhibitory amount of a peptide or antibody of the invention.

In still yet another aspect, this invention provides a method of inhibiting binding of fibrinogen to platelets including the step of contacting platelets with an effective inhibitory amount of a peptide or antibody of the invention.

BRIEF DESCRIPTION OF THE DRAWINGS

In the drawings that form a portion of the specification;

FIG. 6 shows the amino acid residue sequences of a part of the heavy chain of the antibodies of the present invention.

DESCRIPTION OF THE SEQUENCE LISTING

Figure 1:
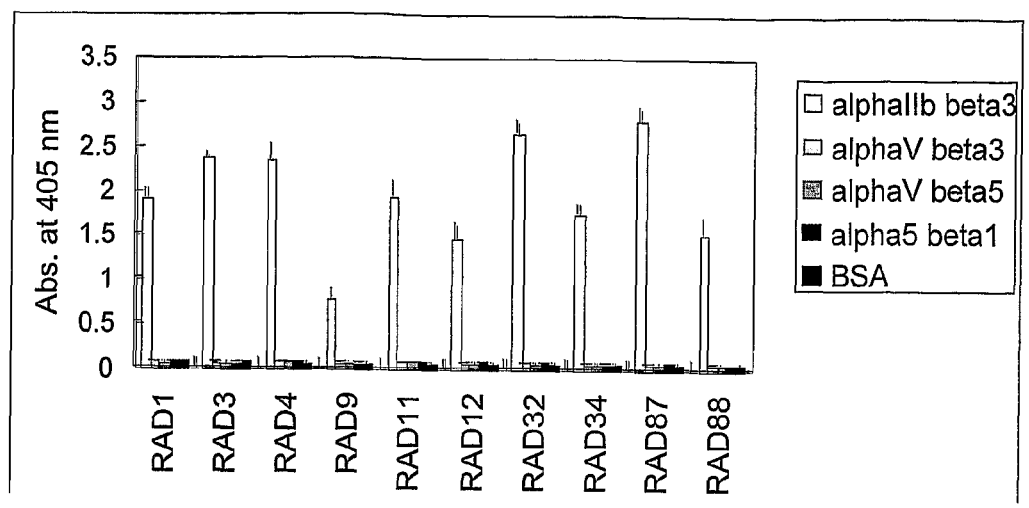
FIG. 1 shows that selected Fabs bind to human integrin $\alpha_{IIb}\beta_3$ but not to other RGD-binding human integrins. Shown are ELISA results based on immobilized human integrins $\alpha_v\beta_3$, $\alpha_v\beta_5$, $\alpha_{IIb}\beta_3$ and $\alpha_5\beta_1$ and supernatant containing soluble Fabs expressed by pComb3X-transfected E. coli. A rat anti-HA mAb conjugated to HRP was used for detection.

The content of the sequence listing information recorded in computer readable form is identical to the written (on paper or compact disc) sequence listing and includes no new matter.

Detailed Description of the Invention

The present invention provides antibodies that immunoreact with integrin $\alpha_{IIb}\beta_3$ The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab') and F(v), single domain antibodies (dAbs), folded immunoglubulin constructs, and active fragments thereof.

An antibody of the present invention is made and identified using phage display technology as is well known in the art (See, for example, International Patent Application Publication WO 94/18221). A detailed description of such procedures is set forth below in the Examples. A preferred antibody is a human antibody. The present invention discloses integrin $\alpha_{IIb}b_3$ specific human mAbs from a newly designed synthetic human antibody library. First, the two cysteine residues present in the previous libraries were removed from HCDR3. The reduction in HCDR3 length along with the removal of the disulfide bridge potentially allows for more structural flexibility in the HCDR3 loop. The removal of the disulfide bridge was encouraged by the observation that a peptide derived from the HCDR3 of a previously selected antibody (CSFGRGDIRNC) (SEQ ID NO:1) and its linear version GSFGRGDIRNG (SEQ ID NO:2) had nearly identical efficacy in ligand binding assays (Smith, J. W., Hu, D., Satterthwait, A., Pinz-Sweeney, S., and Barbas, C. F., 3rd (1994) Building synthetic antibodies as adhesive ligands for integrins. *J Biol Chem* 269, 32788-32795). Second, we chose RAD rather than RGD as the integrin-binding core motif and randomized six residues in the flanking region. An RAD-containing peptide, GRADSP, has been widely used as inactive control peptide in experiments where RGD-containing peptides are tested (Wu, M. H., Ustinova, E., and Granger, H. J. (2001) Integrin binding to fibronectin and vitronectin maintains the barrier function of isolated porcine coronary venules. *J Physiol* 532, 785-791; Slepian, M. J., Massia, S. P., Dehdashti, B., Fritz, A., and Whitesell, L. (1998) Beta3-integrins rather than beta1-integrins dominate integrin-matrix interactions involved in postinjury smooth muscle cell migration. *Circulation* 97, 1818-1827; Guilherme, A., Torres, K., and Czech, M. P. (1998) Cross-talk between insulin receptor and integrin alpha5 beta1 signaling pathways. *J Biol Chem* 273, 22899-22903; Hautanen, A., Gailit, J., Mann, D. M., and Ruoslahti, E. (1989) Effects of modifications of the RGD sequence and its context on recognition by the fibronectin receptor. *J Biol Chem* 264, 1437-1442; Adderley, S. R., and Fitzgerald, D. J. (2000) Glycoprotein IIb/IIIa antagonists induce apoptosis in rat cardiomyocytes by caspase-3 activation. *J Biol Chem* 275, 5760-5766). However, the fact that we selected RAD from our motif optimization library (Smith, J. W., Hu, D., Satterthwait, A., Pinz-Sweeney, S., and Barbas, C. F., 3rd (1994) Building synthetic antibodies as adhesive ligands for integrins. *J Biol Chem* 269, 32788-32795), suggests that the flanking residues determine whether or whether not RAD motifs can bind to integrins. We hypothesized that the RAD motif embedded in a randomized flanking region might increase the probability of selecting antibodies specific for integrin $\alpha_{IIb}\beta_3$.

Here we used phage display to select monoclonal antibodies specific to integrin $\alpha_{IIb}\beta_3$ from a synthetic human antibody library based on the randomized HCDR3 sequence VGXXXRADXXXYAMDV (SEQ ID NO:3). The selected antibodies revealed a strong consensus amino acid sequence in HCDR3 (V(V/W)CRAD(K/R)RC) (exemplified by SEQ ID NOs:4, 5, 6, and 7) and high specificity toward integrin $\alpha_{IIb}\beta_3$ but not to other RGD binding integrins such as integrins $\alpha_v\beta_3$, $\alpha_v\beta_5$, and $\alpha_5\beta_1$. The selected antibodies as well as three synthetic peptides VWCRADRRC (SEQ ID NO:5), VWCRADKRC (SEQ ID NO:6), and VVCRADRRC (SEQ ID NO:7) whose sequences were derived from the HCDR3 sequences of the selected antibodies strongly inhibited the interaction between integrin $\alpha_{IIb}b_3$ and fibrinogen and platelet aggregation ex vivo. To our knowledge these are the first fully human monoclonal antibodies that are specific to integrin $\alpha_{IIb}\beta_3$ and can potently inhibit platelet aggregation.

In one aspect, the present invention provides an isolated and purified peptide inhibitor of platelet aggregation. The peptide has from 9 to about 50 amino acid residues and an amino acid residue sequence that corresponds to V(V/W)CRAD(K/R)RC (exemplified by SEQ ID NOs:4, 5, 6, and 7). The peptide preferably includes the amino acid residue sequence of any of SEQ ID NOs: 5-7 and, more preferably, has the amino acid residue sequence of any of SEQ ID NOs: 5-7. In another aspect, the invention provides an antibody that specifically immunoreacts with integrin $\alpha_{IIb}\beta_3$. The antibody includes the amino acid residue sequence V(R/G)V(V/W)CRAD (R/K)RCYAMDV (exemplified by SEQ ID NOs:8, 25, 26, 26, 28, 29, 30, and 31) within a complementarity determining region of the antibody. Preferably, the complementarity determining region is located in a heavy chain of the antibody and, more particularly, the complementarity determining region is HCDR3. The antibody is most preferably a human antibody. Exemplary and preferred antibodies are designated herein as RAD3, RAD4, RAD9, RAD11, RAD12, RAD32, RAD34, RAD87, or RAD88. The invention also contemplates an antibody having the immunoreactivity of any of RAD3, RAD4, RAD9, RAD11, RAD12, RAD32, RAD34, RAD87, or RAD88.

In yet another aspect, this invention provides a method of inhibiting platelet aggregation including the step of contacting platelets with an effective inhibitory amount of a peptide or antibody of the invention.

In still yet another aspect, this invention provides a method of inhibiting binding of fibrinogen to platelets including the step of contacting platelets with an effective inhibitory amount of a peptide or antibody of the invention.

The present invention describes, in one embodiment, human monoclonal antibodies that contain a binding site as described herein and which bind specifically to a preselected target molecule. The invention also describes cell lines which produce the antibodies, methods for producing the cell lines, and methods for producing the human monoclonal antibodies.

Insofar as a display protein of this invention on a phagemid particle is, in preferred embodiments, a fusion protein between an immunoglobulin heavy or light chain and a filamentous phage membrane anchor, it is to be understood that the display protein is, in effect, an engineered immunoglobulin heavy or light chain into which a binding site has been introduced. Furthermore, in many embodiments, the expression of the display protein is prepared on the phagemid surface as a heterodimer formed between immunoglobulin heavy and light chain peptides, with one or the other being a fusion protein with the membrane anchor. Thus, where the heavy chain is used as the fusion protein, a display protein in preferred embodiments comprises a Fab fragment having an anchored heavy chain associated with a light chain.

The present invention also describes, in one embodiment, polynucleotides that encode human monoclonal antibodies containing a binding site as described herein and which human monoclonal antibodies bind specifically to a preselected target molecule. Polynucleotides that encode for human monoclonal antibodies can be sequenced to identify the polynucleotide sequence. Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Hamilton MICROLAB 2200 (Hamilton, Reno Nev.), Peltier thermal cycler 200 (PTC200; MJ Research, Watertown Mass.) and the ABI CATALYST 800 (Perkin-Elmer). Sequencing is then carried out using either ABI 373 or 377 DNA sequencing systems (Perkin-Elmer), the MEGABACE 1000 DNA sequencing system (Molecular Dynamics, Sunnyvale Calif.), or other systems known in the art. The resulting sequences are analyzed using a variety of algorithms which are well known in the art. (See, for example, Ausubel, F. M. (1997) Short Protocols in Molecular Biology, John Wiley & Sons, New York N.Y., unit 7.7; Meyers, R. A. (1995) Molecular Biology and Biotechnology, Wiley VCH, New York N.Y., pp. 856-853.)

The preparation of cell lines producing monoclonal antibodies of the invention is described in great detail further herein, and can be accomplished using the phagemid vector mutagenesis methods described herein, and using routine screening techniques which permit determination of the elementary binding patterns of the monoclonal antibody of interest indicative that the binding site has been produced. Thus, if a human monoclonal antibody being tested binds to the preselected target molecule, then the human monoclonal antibody being tested and the human monoclonal antibody produced by the cell lines of the invention are considered equivalent.

It is also possible to determine, without undue experimentation, if a human monoclonal antibody has the same (i.e., equivalent) specificity as a human monoclonal antibody of this invention by ascertaining whether the former prevents the latter from binding to a preselected target molecule. If the human monoclonal antibody being tested competes with the human monoclonal antibody of the invention, as shown by a decrease in binding by the human monoclonal antibody of the invention in standard competition assays for binding to the target molecule when present in the solid phase, then it is likely that the two monoclonal antibodies bind to the same, or a closely related, epitope.

Still another way to determine whether a human monoclonal antibody has the specificity of a human monoclonal antibody or peptide of the invention is to pre-incubate the human monoclonal antibody or peptide of the invention with the target molecule with which it is normally reactive, and then add the human monoclonal antibody being tested to determine if the human monoclonal antibody being tested is inhibited in its ability to bind the target molecule. If the human monoclonal antibody being tested is inhibited then, in all likelihood, it has the same, or functionally equivalent, epitopic specificity as the monoclonal antibody or peptide of the invention.

An additional way to determine whether a human monoclonal antibody has the specificity of a human monoclonal antibody of the invention is to determine the amino acid residue sequence of the complementarity determining region (CDR) regions of the antibodies in question. Antibody molecules having identical, or functionally equivalent, amino acid residue sequences in their CDR regions have the same binding specificity. Methods for sequencing peptides are well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence.

Particularly preferred is a human monoclonal antibody having the binding specificity of the monoclonal antibody produced by an *E. coli* microorganism or a fungal microorganism or a hybridoma cell or produced by a plasmid vector as described further herein. Such methods of producing peptides, polypeptides, proteins, and antibodies are well known in the art. Use of the term "having the binding specificity of" indicates that equivalent monoclonal antibodies exhibit the same or similar immunoreaction (binding) properties and compete for binding to a preselected target molecule.

The term "conservative variation" also includes the use of a substituted amino acid in place of an unsubstituted parent amino acid provided that antibodies having the substituted peptide also bind to the preselected target molecule. Analogously, another preferred embodiment of the invention relates to polynucleotides which encode the above noted heavy and/ or light chain peptides and to polynucleotide sequences which are complementary to these polynucleotide sequences. Complementary polynucleotide sequences include those sequences which hybridize to the polynucleotide sequences of the invention under stringent hybridization conditions.

Human monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies.

The invention contemplates, in one embodiment, a monoclonal antibody of this invention produced by the present methods.

In another preferred embodiment, the invention contemplates a truncated immunoglobulin molecule comprising a Fab fragment derived from a human monoclonal antibody of this invention. The Fab fragment, lacking Fc receptor, is soluble, and affords therapeutic advantages in serum half-life, and diagnostic advantages in modes of using the soluble Fab fragment. The preparation of a soluble Fab fragment is generally known in the immunological arts and can be accomplished by a variety of methods. A preferred method of producing a soluble Fab fragment is described herein.

Preferably, an antibody of this invention specifically immunoreacts with integrin $\alpha_{IIb}\beta_3$. That is, an antibody shows preferential binding to integrin $\alpha_{IIb}\beta_3$ as compared to other integrins. Exemplary and preferred antibodies are disclosed herein and designated as RAD3, RAD4, RAD3, RAD4, RAD9, RAD11, RAD12, RAD32, RAD34, RAD87, or RAD88. The amino acid residue sequences of the VH region of those antibodies is set forth in FIG. 6.

Particularly preferred human monoclonal antibodies are those having the immunoreaction (binding) specificity of a monoclonal antibody having heavy (H) and light (L) chain immunoglobulin variable region amino acid residue sequences in pairs (H:L) where the light chain is the light chain described herein and the heavy chain has one of the recited sequences of FIG. 6 and conservative substitutions thereof.

Conservative substitutions are those in which at least one residue in the amino acid sequence has been removed and a different residue inserted in its place. Such substitutions generally are made in accordance with the Table 2 when it is desired to maintain the activity of the protein. Table 2 shows amino acids which can be substituted for an amino acid in a protein and which are typically regarded as conservative substitutions.

TABLE 2

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Substitutions that are less conservative than those in Table 2 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histidyl, is substituted for (or by) an electronegative residue, for example, glutamyl or aspartyl; or (d) a residue having a bulky side chain, for example, phenylalanine, is substituted for (or by) one not having a side chain, for example, glycine.

Various methods such as Scatchard analysis in conjunction with radioimmunoassay techniques may be used to assess the affinity of antibodies for an integrin. Affinity is expressed as an association constant, $K_a$, which is defined as the molar concentration of integrin-antibody complex divided by the molar concentrations of free antigen and free antibody under equilibrium conditions. The $K_a$ determined for a preparation of polyclonal antibodies, which are heterogeneous in their affinities for multiple integrin epitopes, represents the average affinity, or avidity, of the antibodies for integrin. The $K_a$ determined for a preparation of monoclonal antibodies, which are monospecific for a particular integrin epitope, represents a true measure of affinity. High-affinity antibody preparations with $K_a$ ranging from about $10^9$ to $10^{12}$ L/mole are preferred for use in immunoassays in which the integrin-antibody complex must withstand rigorous manipulations. Low-affinity antibody preparations with $K_a$ ranging from about $10^6$ to $10^7$ L/mole are preferred for use in immunopurification and similar procedures which ultimately require dissociation of integrin, preferably in active form, from the antibody. (Catty, D. (1988) Antibodies, Volume I: A Practical Approach, IRL Press, Washington, D.C.; and Liddell, J. E. and Cryer, A. (1991) A Practical Guide to Monoclonal Antibodies, John Wiley & Sons, New York, N.Y.)

Affinity can also be expressed as dissociation constant or $K_d$. Preferred binding affinities include those with a dissociation constant or $K_d$ less than $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M.

In another aspect, the invention provides a peptide that inhibits platelet aggregation. The peptide has from 9 to about 50 amino acid residues and is derived from an antibody of this invention. Preferably, the peptide includes an amino acid residue sequence that corresponds to the formula V(V/W)CRAD(K/R)RC (exemplified by SEQ ID NOs:4, 5, 6, and 7). Exemplary and preferred peptides are set forth below in the examples.

The present invention contemplates therapeutic compositions useful for practicing the therapeutic methods described herein. Therapeutic compositions of the present invention contain a physiologically tolerable carrier together with at least one species of human monoclonal antibody or peptide derived therefrom as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. Thus, an antibody molecule-containing composition can take the form of solutions, suspensions, tablets, capsules, sustained release formulations or powders, or other compositional forms.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the peptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains a human monoclonal antibody of the present invention, typically in an amount of at least 0.1 weight percent of antibody per weight of total therapeutic composition. A weight percent is a ratio by weight of antibody to total composition. Thus, for example, 0.1 weight percent is 0.1 grams of antibody per 100 grams of total composition.

Preferably, an antibody-containing therapeutic composition typically contains about 10 microgram (µg) per milliliter (ml) to about 100 milligrams (mg) per ml of antibody as active ingredient per volume of composition, and more preferably contains about 1 mg/ml to about 10 mg/ml (i.e., about 0.1 to 1 weight percent).

A therapeutic composition in another embodiment contains a peptide of the present invention, typically in an amount of at least 0.1 weight percent of peptide per weight of total therapeutic composition. A weight percent is a ratio by weight of peptide to total composition. Thus, for example, 0.1 weight percent is 0.1 grams of peptide per 100 grams of total composition.

Preferably, a peptide-containing therapeutic composition typically contains about 10 microgram (µg) per milliliter (ml) to about 100 milligrams (mg) per ml of peptide as active ingredient per volume of composition, and more preferably contains about 1 mg/ml to about 10 mg/ml (i.e., about 0.1 to 1 weight percent).

In another aspect, the present invention contemplates therapeutic methods using the compositions and compounds of the invention. In view of the benefit of using human monoclonal antibodies in vivo in human patients, the presently described antibodies are particularly well suited for in vivo use as a therapeutic reagent for blocking or inhibiting the function of the target molecule to which the antibody binds. The peptides derived from the monoclonal antibodies described herein are also contemplated for use in the therapeutic methods of this invention. The method comprises contacting a sample believed to contain the target molecule with a composition comprising a therapeutically effective amount of a human monoclonal antibody or peptide of this invention that binds the target molecule.

For in vivo modalities, the method comprises administering to the patient a therapeutically effective amount of a physiologically tolerable composition containing a human monoclonal antibody or peptide of the invention.

The dosage ranges for the administration of the monoclonal antibodies and peptides of the invention are those large enough to produce the desired effect in which the disease symptoms mediated by the target molecule are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

A therapeutically effective amount of an antibody of this invention is typically an amount of antibody such that when administered in a physiologically tolerable composition is sufficient to achieve a plasma concentration of from about 0.1 microgram (µg) per milliliter (ml) to about 100 µg/ml, preferably from about 1 µg/ml to about 5 µg/ml, and usually about 5 µg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

A therapeutically effective amount of a peptide of this invention is typically an amount of peptide such that when administered in a physiologically tolerable composition is sufficient to achieve a plasma concentration of from about 0.1 microgram (µg) per milliliter (ml) to about 100 µg/ml, preferably from about 1 µg/ml to about 10 µg/ml. Stated differently, the dosage can vary from about 0.1 mg/kg to about 300 mg/kg, and preferably from about 0.2 mg/kg to about 200 mg/kg, in one or more dose administrations daily, for one or several days.

The human monoclonal antibodies or peptides of the invention can be administered parenterally by injection or by gradual infusion over time. Although the target molecule can typically be accessed in the body by systemic administration and therefore most often treated by intravenous administration of therapeutic compositions, other tissues and delivery means are contemplated where there is a likelihood that the tissue targeted contains the target molecule. Thus, human monoclonal antibodies or peptides of the invention can be administered intravenously, intraperitoneally, intramuscularly, subcutaneously, intracavity, transdermally, and can be delivered by peristaltic means.

The therapeutic compositions containing a human monoclonal antibody or a peptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient to be administered depend on the judgment of the practitioner and are peculiar to, each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges' specified for in vivo therapies are contemplated.

An anti-integrin $\alpha_{IIb}\beta_3$ human monoclonal antibody or peptide derived therefrom containing an integrin $\alpha_{IIb}\beta_3$-binding site can be used to in vivo or in vitro modulate the function of integrin $\alpha_{IIb}\beta_3$ on platelets. For instance, the human monoclonal antibody or peptide can be used in a pharmaceutically acceptable composition that, when administered to a human subject in an effective amount, is capable of inhibiting the aggregation of platelets, and thereby decreasing the rate of thrombus formation. Thus, in vivo administration of an anti-integrin $\alpha_{IIb}\beta_3$ human monoclonal antibody that inhibits platelet aggregation can be used in vivo to modulate any physiological response initiated by platelet adhesion, such as coagulation and some inflammatory responses.

When this method is carried out in vivo, an effective amount of an antibody or peptide composition containing a physiologically tolerable diluent and antibody molecules that immunoreact with integrin $\alpha_{IIb}\beta_3$ and that inhibit platelet aggregation is intravenously administered to a mammal, and the mammal is maintained for a sufficient time period to allow the antibody molecules to immunoreact with any integrin $\alpha_{IIB}\beta_3$ present and form an immunoreaction product and to allow the binding site containing the peptide to bind to integrin $\alpha_{IIB}\beta_3$ and form a peptide-receptor complex such that the normal ligand can no longer bind to the receptor.

The integrin $\alpha_{IIB}\beta_3$-specific antibodies of this invention are useful as antithrombotic therapeutic agents. The antibodies (or fragments thereof) can be used to inhibit platelet aggregation and thrombus formation. The antibodies can also be used to inhibit cyclic flow variations which are caused by platelet aggregation, and which may precede thrombus formation or reformation. The antibodies can be used in a variety of situations where thrombus formation or reformation (reocclusion) is to be prevented. For instance, the antibody can be administered to an individual (for example, a mammal such as a human) to prevent thrombosis in pulmonary embolism, transient ischemic attacks (TIAs), deep vein thrombosis, coronary bypass surgery, surgery to insert a prosthetic valve or vessel (for example, in autologous, non-autologous or synthetic vessel graft). The antibodies of the present invention can also be administered to an individual to prevent platelet aggregation and thrombosis in angioplasty procedures performed by balloon, coronary atherectomy, laser angioplasty or other suitable methods. Antibody can be administered prior to the angioplasty procedure (pre-angioplasty), during angioplasty, or post-angioplasty. Such treatment can prevent thrombosis and thereby reduce the rate of thrombotic complications following angioplasty, such as death, myocardial infarction, or recurrent ischemic events necessitating PTCA or coronary bypass surgery.

The aggregation of platelets activates the coagulation cascade and produces a more stable fibrin meshwork and occlusive clot, which can be lysed by thrombolytic agents. The antibody can be administered to an individual (for example, a human) alone or in conjunction with a thrombolytic agent, such as a plasminogen activator (for example, tissue plasminogen activator, urokinase, or streptokinase, recombinant tissue plasminogen activator) or an anticoagulant or anti-platelet agent, such as aspirin, heparin, or a coumarin anticoagulant (for example, warfarin), to prevent or reduce reocclusion that can occur after thrombolysis and to accelerate clot lysis. The antibody or fragment can be administered before, along with or subsequent to administration of the thrombolytic agent or anticoagulant, in amounts sufficient to prevent platelet aggregation that can result in reocclusion.

An effective amount (for example, an amount sufficient for inhibition of platelet aggregation and thereby of inhibition of thrombus formation) of the antibody or antibody fragment can be given parenterally, preferably intravenously, in a pharmaceutically acceptable vehicle such as sterile saline. Buffered media may be included. The antibody formulation can contain additional additives, such as a stabilizer (for example, Polysorbate 80, USP/NF). The antibody can be administered in a single dose, continuously, or in multiple infusions (for example, a bolus injection, followed by continuous infusion). Alternatively, the antibody could be administered by a controlled release mechanism (for example, by a polymer or patch delivery system) or by another suitable method. The amount to be administered will depend on a variety of factors such as the clinical symptoms, weight of the individual, whether other drugs (for example, thrombolytic agents) are administered.

The integrin $\alpha_{IIB}\beta_3$-specific immunoglobulins of this invention are also useful for thrombus imaging. For this purpose, antibody fragments are generally preferred. As described above, chimeric heavy chain gene can be designed in truncated form to produce a chimeric immunoglobulin fragment (for example, Fab, Fab', or F(ab')$_2$) for immunoscintigraphic imaging. These molecules can be labeled either directly or through a coupled chelating agent such as DTPA, with radioisotopes such as $^{131}$Iodine, $^{125}$Iodine, $^{99}$Technetium, or $^{111}$Indium to produce radioimmunoscintigraphic agents. Alternatively, a radiometal binding (chelating) domain can be engineered into the chimeric antibody site to provide a site for labeling. Thus, an immunoglobulin can be designed as a protein that has a nonhuman platelet-specific variable region, a human constant region (preferably truncated), and a metal binding domain derived from a metal binding protein, such as metallothionein.

The integrin $\alpha_{IIB}\beta_3$-specific immunoglobulin is administered to a patient suspected of having thrombus. After sufficient time to allow the labeled immunoglobulin to localize at the thrombus site, the signal generated by the label is detected by a photoscanning device such as a gamma camera. The detected signal is then converted to an image of the thrombus. The image makes it possible to locate the thrombus in vivo and to devise an appropriate therapeutic strategy.

The Examples that follow illustrate exemplary embodiments of the present invention and are not limiting of the specification or claims in any way.

EXAMPLES

Cell Line, Proteins, and Peptides.

Human umbilical vein endothelial cells (HUVEC) were purchased from Biowhittaker (Walkersville, Mass.) and were grown in EGM-2 medium (Biowhittaker) supplied with the cells. Integrin $\alpha_{IIB}\beta_3$ was purchased from Enzyme Research Laboratories (South Bend, Ind.). Integrins $\alpha_v\beta_3$, and $\alpha_v\beta_5$ were from Chemicon (Temecula, Calif.). Human fibrinogen was purchased from Sigma-Aldrich (St. Louis, Mo.). Peptides used in this study were synthesized by Peptron (Taejon, Korea). Human fibrinogen and peptides were biotinylated using EZ-Link-PFP-biotin (Pierce, Rockford, Ill.) following instructions by the manufacturer. Abciximab (ReoPro) was purchased from Eli Lilly (Indianapolis, Ind.).

Library Generation.

Total RNA was prepared from bone marrow of six healthy donors using TRI REAGENT (Molecular Research Center, Cincinnati, Ohio). First strand cDNA was synthesized using the SUPERSCRIPT Preamplification System with oligo(dT) priming (Life Technologies, Gaithersburg, Md.). A cDNA fragment encoding part of FR3, randomized HCDR3, and FR4 of $V_H$ fused to $C_H1$ were amplified by PCR using primers neo-rad-f (GTG TAT TAC TGT GCG AGA GTG GGG NNK NNK NNK CGT GCC GAC NNK NNK NNK TAC GCT ATG GAC GTC TGG GGC) (SEQ ID NO:9) and dpseq (AGAAGC GTA GTC CGG AAC GTC) (SEQ ID NO:10)

and phagemid vector pComb3X-TT (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.) as template. For amplification of the cDNA fragment encoding FR1 to FR3 of $V_H$, the prepared human bone marrow cDNA was subjected to PCR using primers DP-47N-term (GCT GCC CAA CCA GCC ATG GCC GAG GTG CAG CTG TTG GAG TCT GGG GGA GGC TTG GTA) (SEQ ID NO:11) and DP-47FR3 (CAC TCT CGC ACA GTAATA CAC GGC CGT GTC CTC GGC TCT) (SEQ ID NO:12). All amplifications were performed under standard PCR conditions using Taq polymerase (Pharmacia, Piscataway, N.J.). The two cDNA fragments were assembled by overlap extension PCR using primers lead-VH (GGC CAT GGC TGG TTG GGC AGC) (SEQ ID NO:13) and dp-Ex (GAG GAG GAG GAG GAG GAG AGA AGC GTA GTC CGG AAC GTC) (SEQ ID NO:14). A previously selected DPK-26 human kappa light chain cDNA in phagemid vector pComb3X was amplified by PCR using primers ompseq (AAG ACA GCT ATC GCG ATT GCA GTG) (SEQ ID NO:15) and leadB (GGC CAT GGC TGG TTG GGC AGC) (SEQ ID NO:16). The cDNAs encoding the heavy chain fragment library and the light chain were fused by overlap extension PCR using primers ompseq and dp-Ex. The resulting Fab encoding library was digested with Sfi I (Roche, Indianapolis, Ind.), ligated into phagemid vector pComb3X, and transformed into *E. coli* strain ER2537 (New England Biolabs, Beverly, Mass.) as described (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.).

Library Selection.

A total of seven rounds of panning (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.) were performed. First, five rounds of panning against immobilized human integrin $\alpha_{IIb}\beta_3$ were carried out using 100 ng of protein in 50 µl of metal buffer (25 mM Tris-HCl, pH 7.5, 137 mM NaCl, 1 mM KCl, 1 mM $MgCl_2$, 1 mM $CaCl_2$, and 1 mM $MnCl_2$) for coating, 0.05% Tween20 in TBS (Tris-buffered saline) for washing, and 10 mg/ml trypsin (Becton-Dickson, Franklin Lakes, N.J.) in TBS for elution. Costar 3690 96-well plates (Corning, N.Y.) were used for panning. Trypsinization was done for 30 min at 37° C. For the sixth round of panning, 25 ng of protein in metal buffer was used for coating and 0.5% Tween20 in TBS was used for washing. For the seventh round of panning, 12.5 ng of protein was used for coating. The plate was washed five times in the first round, ten times in the second and third round, and 15 times in the remaining four rounds. The output phage pool of each round was monitored by phage ELISA using sheep anti-M13 conjugated to horseradish peroxidase (Pharmacia) as a secondary antibody. After the last round of panning, phage were produced from single clones grown on output plates and tested for binding to integrin $\alpha_{IIb}\beta_3$ by phage ELISA as described (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.).

Light Chain Shuffling and Selection.

$V_\kappa$ and $V_\lambda$ encoding cDNAs were amplified from the prepared human bone marrow cDNA using a previously published panel of primers (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.), comprising sense primers that hybridize to sequences that encode the N-terminal amino acids of the various $V_\kappa$ and $V_\lambda$ families and reverse primers that hybridize to sequences that encode the C-terminal amino acids of FR4 of $V_\kappa$ and $V_\lambda$ respectively, which are highly conserved (Kabat, E. A., Wu, T. T., Perry, H. M., Gottesman, K. S., and Foeller, C. (1991) *Sequences of Proteins of Immunological Interest*, U.S. Department of Health and Human Services, Public Health Service, Natl. Inst. Health, Bethesda). $C_\kappa$ and $C_\lambda$ encoding sequences were prepared as described (Barbas, C. R, 3rd, Burton, D. R., Scott, J. K., and Silverman, G. J. (2001) *Phage Display: A Laboratory Manual*, Cold Spring Harbor Laboratory Press, Cold Spring Harbor, N.Y.) and fused to $V_\kappa$ and $V_\lambda$ encoding sequences respectively, by overlap extension PCR using primers RSC-F (GAG GAG GAG GAG GAG GAG GCG GGG CCC AGG CGG CCG AGC TC) (SEQ ID NO:17) and lead-B (GGC CAT GGC TGG TTG GGC AGC) (SEQ ID NO:18). Two cloning strategies were used to replace the DPK-26 human kappa light chain in the selected Fab. In one approach, the DPK-26 human kappa light chain cDNA was removed from the phagemid vector pool obtained after the last round of panning by restriction digestion with Sac I and Xba I (New England Biolabs). Then the human light chain encoding library was digested with the same restriction enzymes, ligated into the prepared phagemid vector, and transformed into *E. coli* strain ER2537. In the second approach, heavy chain fragment encoding cDNA was amplified from the phagemid vector pool obtained after the last round of panning using lead-VH and dpseq primers and fused with the human light chain encoding library by overlap extension PCR using primers ompseq and dp-EX. The resulting Fab encoding library was digested with Sfi I, ligated into phagemid vector pComb3X, and transformed into *E. coli* strain ER2537 as described previously (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.). After mixing the two light chain libraries, three rounds of panning, each with 12.5 ng coated human integrin $\alpha_{IIb}\beta_3$ were performed. The plate was washed 15 times in each round. After the last round of panning, phage were produced from single clones grown on output plates and tested for binding to integrin $\alpha_{IIb}\beta_3$ by phage ELISA as described (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.).

ELISA.

For production of soluble Fab, published procedures were followed (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.). Briefly, selected colonies were allowed to grow in 5 ml of superbroth for 6 h at 37° C. Growth was continued overnight after adding IPTG (isopropyl-beta-D-thiogalactopyranoside, Sigma-Aldrich) to a final concentration of 1 mM. For each well on a Costar 3690 96-well plate, 100 ng of integrin $\alpha_{IIb}\beta_3$ in 50 µl metal buffer was coated at 4° C. overnight. The plate was blocked by adding 3% (w/v) skim milk in TBS followed by incubation for 1 h at 37° C. Subsequently, 50 µl of the culture supernatant diluted with the same volume of 3% (w/v) skim milk in TBS, 50 µl of horseradish peroxidase conjugated rat anti-HA mAb 3F10 (Roche) diluted to 1 µg/ml in 3% skim milk in TBS, and 50 µl of ABTS substrate solution (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.) were added sequentially. Before adding the reagents, the plate was washed five times with 0.05%

Tween20 in TBS. The plate was incubated for 1 h at 37° C. in each step. To check for crossreactivity of the selected Fab, parallel assays with coated integrins $\alpha_v\beta_3$, $\alpha_v\beta_5$, and $\alpha_5\beta_1$ were performed using the same conditions as described above.

Fibrinogen Binding Inhibition Assay.

Wells of a Costar 3690 96-well plate were coated with 100 ng of integrin $\alpha_{IIb}\beta_3$ in 50 µl metal buffer at 4° C. overnight. The plate was washed twice with water and blocked with 160 µl of 3% (w/v) skim milk in TBS for 1 h at 37° C. After the plate was briefly washed with water, 50 µl of culture supernatant containing Fab, purified Fabs RAD87 and Abciximab, or synthetic peptides mixed with 50 µl of 1.2 µM biotinylated fibrinogen in 3% (w/v) skim milk in TBS were added to each well. The final concentrations were adjusted between $1.3 \times 10^{-8}$ M and $8.0 \times 10^{-7}$ M of Fabs and between $8.9 \times 10^{-8}$ M and $9.1 \times 10^{-5}$ M of synthetic peptides. After incubation for 2 h at 37° C. followed by ten times washing with water and five times washing with 0.05% Tween20 in TBS, 50 µl of 0.5 µg/ml streptavidine-HRP (Pierce) diluted in 3% (w/v) skim milk in TBS was added and incubated for 1 h at 37° C. After washing as above, 50 µl of ABTS substrate solution (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.) was added. This experiment was repeated three times at each concentration to get the mean value and standard deviation.

Flow Cytometry.

Peripheral blood was drawn from a healthy volunteer and collected in an ACD tube (Becton Dickinson, San Jose, Calif.). HUVEC were treated for 5 min with 0.05% (w/v) trypsin, 0.53 mM EDTA (Life Technologies), collected by centrifugation at 500 g for 2 mM, and resuspended in 1% (w/v) BSA in PBS (phosphate buffered saline). Subsequently, Fab RAD87 or Fab Abciximab was added to the cells resuspended in 40 µl of 1% (w/v) BSA in PBS or 40 µl periperal blood to reach a final concentration of 0.2 µM. After incubation for 40 min at room temperature followed by washing twice with 1% (w/v) BSA in PBS, 10 µl of FITC conjugated anti-human IgG polyclonal antibodies (Sigma-Aldrich) diluted in 750 µl of 1% (w/v) BSA in PBS was added and incubated for 20 min at room temperature. After washing twice with 1% (w/v) BSA in PBS, flow cytometry was performed using a FACStar instrument from Becton Dickinson (San Jose, Calif.).

Platelet Aggregation Assay.

Peripheral human blood was collected as described above. Platelet-rich plasma (PRP) was obtained from the collected peripheral blood by centrifugation at 135 g for 15 min. Subsequent centrifugation at 1,500 g for 15 min yielded platelet-poor plasma (PPP). By mixing PRP and PPP, conditioned plasma of 300,000-350,000 platelets per 1 µl of plasma was prepared. To 435 µl of the conditioned plasma, RAD 87 mAbs, abciximab and peptides dissolved in 15 µl of PBS were added to final concentrations between 20 nM and 100 nM of mAbs and between 0.4 µM and 90 µM of peptides. The platelet aggregation assay was done as described previously (Klinkhardt, U., Kirchmaier, C. M., Westrup, D., Breddin, H. K., Mahnel, R., Graff, J., Hild, M., and Harder, S. (2000) Differential in vitro effects of the platelet glycoprotein IIb/IIIa inhibitors abximicab or SR121566A on platelet aggregation, fibrinogen binding and platelet secretory parameters. *Thromb Res* 97, 201-207) using a whole blood lumi-aggregometer (Chrono-log, Havertown, Pa.). The impedance of each sample was monitored until a stable baseline was established (<5 mV drift per minute). To induce platelet aggregation, 9 µl of an ADP solution was added to reach a final concentration of 20 µM. Increase in impedance across a pair of electrodes over time was transmitted through an interface to a personal computer for analysis (AGGRO/LINK, Chrono-log).

Affinity Measurement.

The dissociation constant of Fabs RAD87 and abciximab toward integrin $\alpha_{IIb}\beta_3$ was determined with competitive ELISA as described previously (Djavadi-Ohaniance, L., Goldberg, M. E., and Firguet, B. (1996) Measuring antibody affinity in solution. In *Antibody Engineering* (McCafferty, J., Hoogenboom, H. R., and Chiswell, J., eds) pp. 77-98, IRL Press, Oxford; Yi, K., Chung, J., Kim, H., Kim, I., Jung, H., Kim, J., Choi, I., Suh, P., and Chung, H. (1999) Expression and characterization of anti-NCA-95 scFv (CEA 79 scFv) in a prokaryotic expression vector modified to contain a Sfi I and Not I site. *Hybridoma* 18, 243-249). Briefly, wells of a Costar 3690 96-well plate were coated with 250 ng of integrin $\alpha_{IIb}\beta_3$ in 50 µl of metal buffer at 4° C. overnight. The plate was washed five times with water and blocked with 160 µl of 2% BSA in PBS for 2 hr at 37° C. Purified Fab RAD87 or Fab abciximab was mixed with integrin $\alpha_{IIb}\beta_3$ to reach a final concentration of $2 \times 10^{-10}$ M. The final concentrations of integrin $\alpha_{IIb}\beta_3$ were adjusted between $1 \times 10^{-7}$ M and $1 \times 10^{-10}$ M. These mixtures were incubated overnight to allow equilibration. After the plate was briefly washed with water, the antibody-antigen mixtures were added to the wells and incubated for 2 h at room temperature. The plate was washed three times with 0.05% Tween20 in PBS before adding 200 ng/ml horseradish peroxidase conjugated anti-human IgG antibody (Pierce). After incubation at room temperature for 1 h, the plate was washed five times with 0.05% Tween20 in PBS before adding 50 µl of ABTS substrate solution (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.). After incubation at 37° C. for 2 h, the reaction was stopped by adding 50 µl of 3 N HCl. The absorbance of each well was measured at 405 nm in an ELISA plate reader. A Scatchard plot was drawn with υ/[Ag] on the y axis and υ on the x axis. [Ag] is the concentration of the free antigen; u is the fraction of bound antibody, which was obtained by dividing the absorbance in the presence of a defined concentration of soluble antigen by the absorbance in the absence of soluble antigen. The slope of a straight line in the Scatchard plot is equal to $1/K_d$.

Generation and Selection of a Hybrid Naïve/Synthetic Human Fab Library.

The goal of this study was to generate synthetic human antibodies that discriminate integrin $\alpha_{IIb}\beta_3$ from other RGD-binding integrins, especially integrin $\alpha_v\beta_3$, by grafting an RAD motif flanked on both sites by three randomized amino acid residues into HCDR3. First, we used an RAD motif rather than an RGD motif as central recognition sequence. Second, a $CX_9C$ disulfide bridge surrounding the central recognition sequence in both previous studies was removed. Third, the synthetic HCDR3 library was grafted into a naïve human VH library amplified from human bone marrow cDNA. Thus, in addition to its randomization in HCDR3, a second level of library complexity was introduced by diversifying VH.

A human antibody library with the randomized HCDR3 sequence VGXXXRADXXXYAMDV (SEQ ID NO:3), in which X stands for any of the 20 common natural amino acids, was generated in phagemid vector pComb3X. VH, the FR1 to FR3 encoding fragment of the heavy chain variable domain, was amplified by PCR using human variable heavy chain gene DP-47 specific primers and human bone marrow cDNA from six healthy donors as template. This hybrid naïve/ synthetic heavy chain fragment library was initially paired with a previously selected DPK-26 human kappa light chain. The resulting Fab library was cloned into phagemid vector pComb3X, yielding a complexity of $1 \times 10^9$ independent transformants. Randomly chosen clones from the unselected library confirmed the intended variety in VH and HCDR3 sequences. After seven rounds of panning on immobilized human integrin $\alpha_{IIb}\beta_3$, over 80% of the selected clones bound to integrin $\alpha_{IIb}\beta_3$ as analyzed by phage ELISA (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.).

The selected heavy chain fragment encoding sequences were subjected to a second selection step based on light chain shuffling. For this, the DPK-26 human kappa light chain was replaced by a human kappa and lambda light chain library amplified from the human bone marrow cDNA. The resulting naïve human light chain library was again cloned into phagemid vector pComb3X, yielding a complexity of $7 \times 10^8$ independent transformants. After three rounds of panning on immobilized human integrin $\alpha_{IIb}\beta_3$, all selected clones bound to integrin $\alpha_{IIb}\beta_3$ as analyzed by phage ELISA.

Ten individual clones that revealed the strongest binding were subsequently analyzed by DNA sequencing. All but one clone contained a disulfide bridge constrained loop in HCDR3 with the consensus sequence V(V/W)CRAD(K/R)RC (SEQ ID NO:4) (Table 2). The exception, clone RAD1, had the corresponding sequence THSRADRRE (SEQ ID NO:19) (Table 2). All clones revealed a DP-47 VH heavy chain fragment. Whereas four clones had the original DPK-26 human kappa light chain, six clones revealed human kappa or lambda light chains derived from the naïve human light chain library.

Biochemical and Functional Characterization of Selected Human Fabs.

Fabs expressed from the ten selected clones were tested for their reactivity with RGD-binding integrins by ELISA. All Fabs strongly bound to human integrin $\alpha_{IIb}\beta_3$ but not to human integrins $\alpha_v\beta_3$, $\alpha_5\beta_1$ and $\alpha_v\beta_5$ (FIG. 1). To check their reactivity toward native integrin $\alpha_{IIb}\beta_3$ expressed on the surface of human platelets surface, all Fabs were subsequently analyzed by flow cytometry. All selected Fabs were found to bind to human platelets while irrelevant Fabs did not. As the interaction between integrin $\alpha_{IIb}\beta_3$ and fibrinogen is in part mediated by the RGD motif, we tested next whether the selected Fabs could inhibit this protein-protein interaction. For this purpose, we established a competitive ELISA assay based on immobilized integrin $\alpha_{IIb}\beta_3$, biotinylated fibrinogen, and avidin-HRP. The selected Fabs were mixed with the biotinylated fibrinogen at different concentrations and subsequently incubated with the immobilized integrin $\alpha_{IIb}\beta_3$. Avidin-HRP was used to detect biotinylated fibrinogen bound to immobilized integrin $\alpha_{IIb}\beta_3$. All selected Fabs revealed a potent inhibition of the interaction of integrin $\alpha_{IIb}\beta_3$ and fibrinogen.

Figure 2:
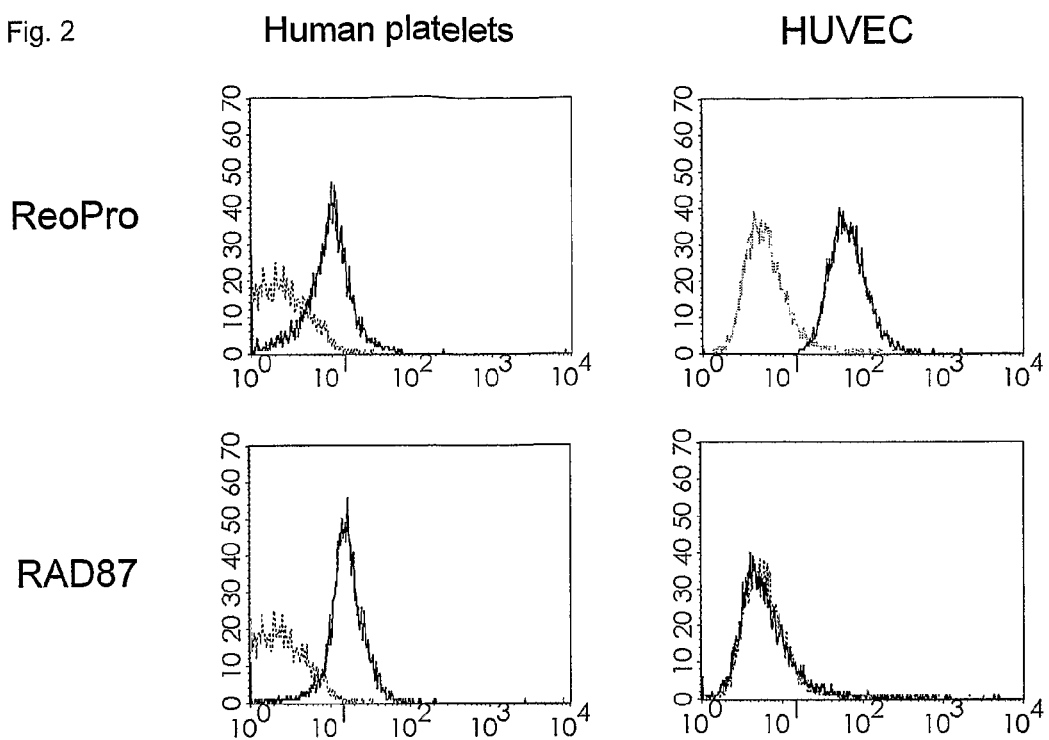
FIG. 2 shows that Fab RAD87 binds to human platelets but not to human umbilical vein endothelial cells (HUVEC). Analysis by flow cytometry showed that Fab RAD87 bound only to human platelets, which express both integrin $\alpha_v\beta_3$ and $\alpha_{IIb}\beta_3$, but not to HUVEC cells, which mainly express integrin $\alpha_v\beta_3$. By contrast, Fab abciximab bound to both platelets and HUVEC cells, confirming its documented cross-reactivity with the two $\beta_3$ integrins. They axis gives the number of events in linear scale, the x axis the fluorescence intensity in logarithmic scale.
Figure 3:
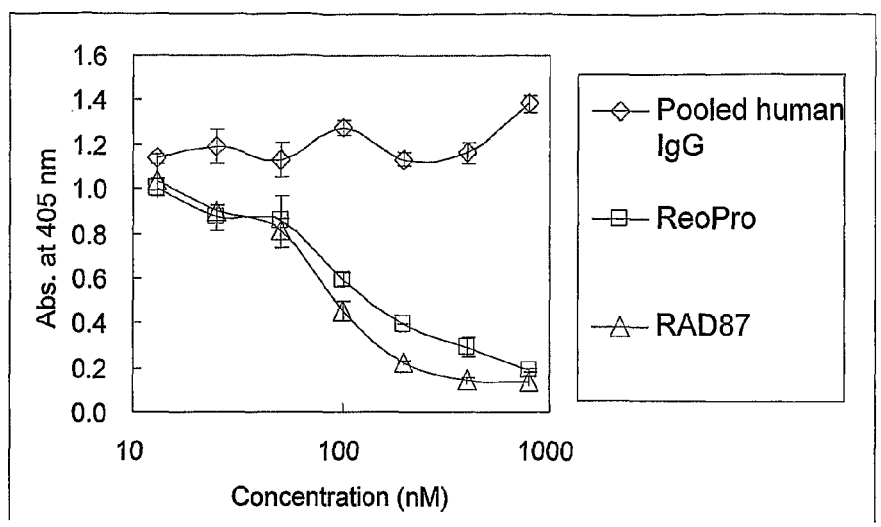
FIG. 3 shows that Fab RAD87 and synthetic peptides derived from the selected HCDR3 sequences inhibit the interaction between integrin $\alpha_{IIb}\beta_3$ and fibrinogen. Biotinylated fibrinogen was mixed with (A) various concentrations of Fabs RAD87 and abciximab as well as pooled human IgG as negative control and (B) synthetic peptides and added to integrin $\alpha_{IIb}\beta_3$ immobilized on an ELISA plate. Streptavidin-HRP was used for detection. Mean values and standard deviations of three independent experiments are shown.
Figure 3:
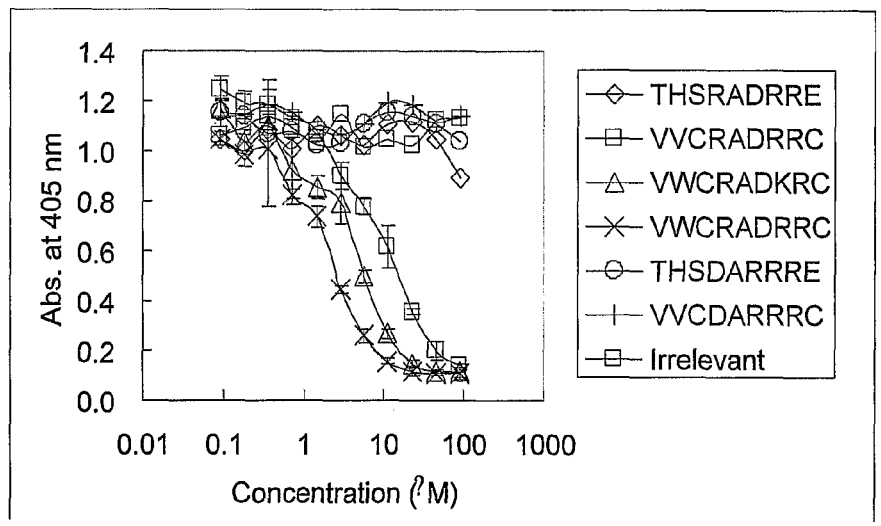

We subsequently focused on Fab RAD87, which showed the strongest binding to integrin $\alpha_{IIb}\beta_3$ (FIG. 1). Fab RAD87 was expressed in *E. coli* and purified as described previously (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.). As revealed by flow cytometry, Fab RAD87 bound only to human platelets but not to HUVEC cells, which mainly express integrin $\alpha_v\beta_3$ (FIG. 2). By contrast, Fab abciximab (ReoPro, Eli Lilly, Indianapolis, Ind.) bound to both platelets and HUVEC cells (FIG. 2), confirming its documented cross-reactivity with the two $\beta_3$ integrins (Bougie, D. W., Wilker, P. R., Wuitschick, E. D., Curtis, B. R., Malik, M., Levine, S., Lind, R. N., Pereira, J., and Aster, R. H. (2002) Acute thrombocytopenia after treatment with tirofiban or eptifibatide is associated with antibodies specific for ligand-occupied GPIIb/IIIa. *Blood* 100, 2071-2076). Fab RAD87 blocked the interaction between integrin $\alpha_{IIb}\beta_3$ and fibrinogen in a dose-dependent manner with an $IC_{50}$ of $8.0 \times 10^{-8}$M. In a parallel experiment, Fab abciximab revealed an $IC_{50}$ of $9.0 \times 10^{-8}$M (FIG. 3A, Table 3). Based on competitive ELISA (Suzuki, K., Sato, K., Kamohara, M., Kaku, S., Kawasaki, T., Yano, S., and Iizumi, Y. (2002) Comparative studies of a humanized anti-glycoprotein IIb/IIIa monoclonal antibody, YM337, and abciximab on in vitro antiplatelet effect and binding properties. *Biol Pharm Bull* 25, 1006-1012; Co, M. S., Yano, S., Hsu, R. K., Landolfi, N. F., Vasquez, M., Cole, M., Tso, J. T., Bringman, T., Laird, W., Hudson, D., and et al. (1994) A humanized antibody specific for the platelet integrin gpIIb/IIIa. *J Immunol* 152, 2968-2976), the $K_d$ value of the monovalent Fab RAD87/integrin $\alpha_{IIb}\beta_3$ interaction was $3.3 \times 10^{-9}$ M (Table 3). The same assay yielded a $K_d$ value of $1.1 \times 10^{-9}$ M for the monovalent Fab abciximab/integrin $\alpha_{IIb}\beta_3$ interaction, as compared to published $6.2 \times 10^{-9}$ M (Table 3) (Tam, S. H., Sassoli, P. M., Jordan, R. E., and Nakada, M. T. (1998) Abciximab (ReoPro, chimeric 7E3 Fab) demonstrates equivalent affinity and functional blockade of glycoprotein IIb/IIIa and alpha(v)beta3 integrins. *Circulation* 98, 1085-1091).

Figure 4:
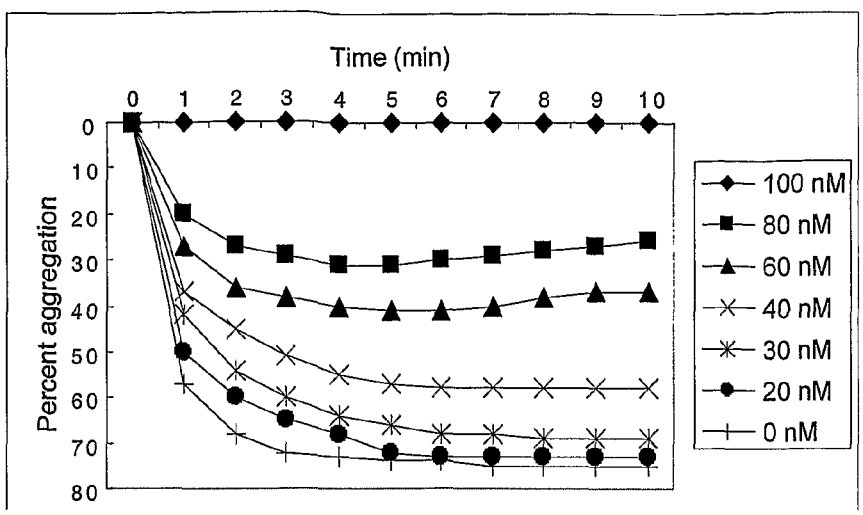
FIG. 4 shows that Fab RAD87 inhibits platelet aggregation ex vivo. The shown platelet aggregation assays were derived from a whole blood lumi-aggregometer. For each assay, 15 µl of Fab RAD87 (A) or Fab abciximab (B) solution was mixed with 435 µl of platelet-rich plasma to reach a final concentration between 20 nM and 100 nM. ADP was then added to a final concentration of 20 µM and the aggregation was monitored for 10 minutes. The plotted mean values and standard deviations of three independent experiments are shown in (C).
Figure 4:
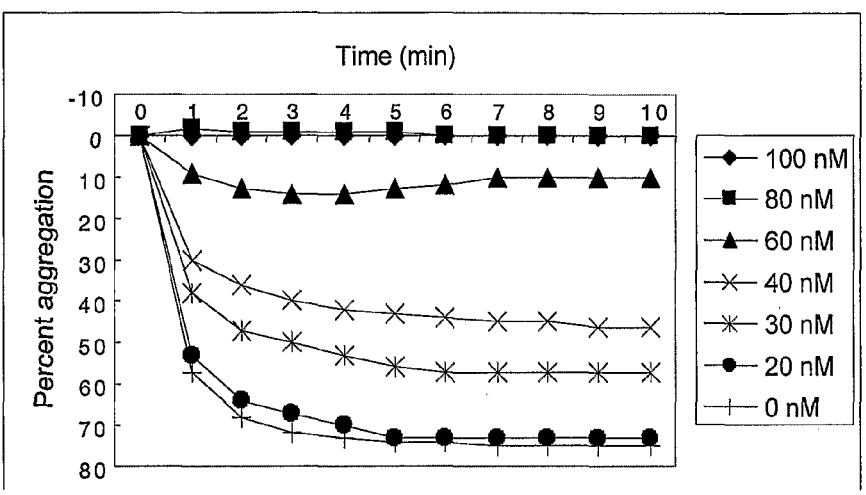
Figure 4:
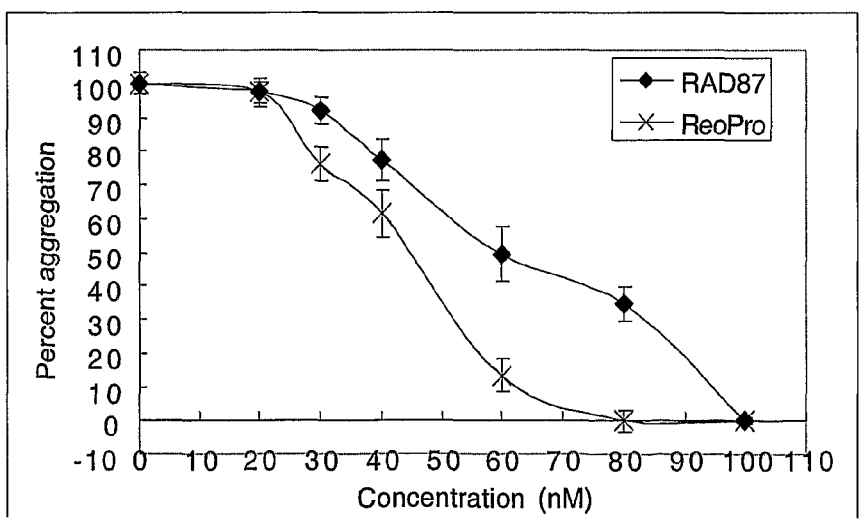

As the interaction between integrin $\alpha_{IIb}\beta_3$ and fibrinogen is an essential step for platelet aggregation, we tested next whether Fab RAD87 could inhibit platelet aggregation ex vivo. Platelet aggregation was induced and monitored by a platelet aggregometer by adding ADP to a final concentration of 20 μM to conditioned plasma prepared from human peripheral blood. Fab RAD87 was found to potently inhibit platelet aggregation with an $EC_{50}$ of 60 nM or 3 μg/ml (FIG. 4; Table 3). In a parallel experiment, the $EC_{50}$ of Fab abciximab was determined to be 45 nM, which was previously reported to be 34 nM (Klinkhardt, U., Kirchmaier, C. M., Westrup, D., Breddin, H. K., Mahnel, R., Graff, J., Hild, M., and Harder, S. (2000) Differential in vitro effects of the platelet glycoprotein IIb/IIIa inhibitors abxicimab or SR121566A on platelet aggregation, fibrinogen binding and platelet secretory parameters. *Thromb Res* 97, 201-207) when platelet aggregation was induced at a concentration of 5 μM ADP.

Biochemical and Functional Characterization of Synthetic Peptides Derived from the Selected HCDR3 Sequences.

Four nonapeptides whose sequences were derived from the selected HCDR3 sequences of the integrin $\alpha_{IIB}\beta_3$ binding Fab were chemically synthesized. This panel included three cyclic peptides, VWCRADKRC (SEQ ID NO:6), VWCRADRRC (SEQ ID NO:5), and VVCRADRRC (SEQ ID NO:7), and linear peptide THSRADRRE (SEQ ID NO:19). Using the competitive ELISA assay described above, all cyclic peptides were found to inhibit the interaction between integrin $\alpha_{IIb}\beta_3$ and fibrinogen in micromolar concentration range. The linear peptide as well as three control peptides—two with an inversed RAD motif, VVCDARRRC (SEQ ID NO:20) and THSDARRRE (SEQ ID NO:21), and one with an unrelated sequence—did not inhibit the protein-protein interaction in the same concentration range (FIG. 3B). The $IC_{50}$ of the most potent cyclic peptides, VWCRADRRC (SEQ ID NO:5) and VWCRADKRC (SEQ ID NO:6) were determined to be $1.2 \times 10^{-6}$ M and $4.2 \times 10^{-6}$ M respectively. The $IC_{50}$ of the cyclic peptide VVCRADRRC whose sequence was derived from Fab RAD87 was $1.1 \times 10^{-5}$ M, which is two orders of magnitude higher than the corresponding $IC_{50}$ obtained for Fab RAD87 (FIG. 3B).

Figure 5:
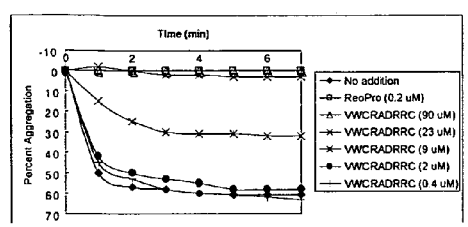
FIG. 5 shows that synthetic peptides derived from the selected HCDR3 sequences inhibit platelet aggregation ex vivo. Platelet aggregation assays were performed as described in FIG. 4 in the presence of the indicated peptide concentrations. Note that all three cyclic peptides with the RAD motif potently inhibited platelet aggregation (A-C) whereas a linear peptide with the RAD motif and two control peptides with an inversed RAD motif have no effect over background (D). Abciximab Fab was used as positive control in all platelet aggregation assays.
Figure 5:
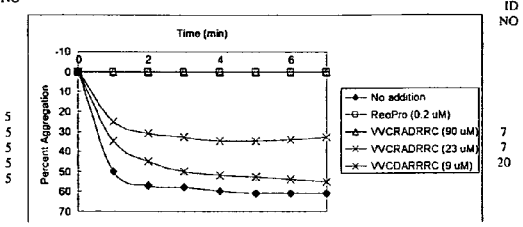
Figure 5:
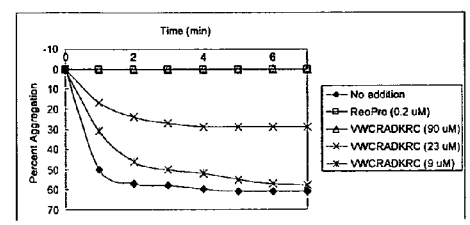
Figure 5:
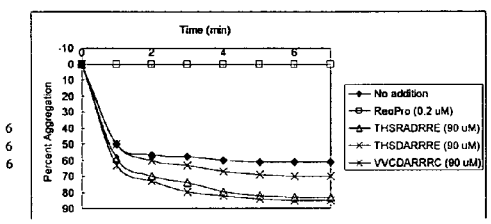

FIG. 5 shows the ex vivo platelet aggregation assay in the presence of various concentrations of VWCRADRRC (SEQ ID NO:5) (A), VVCRADRRC (SEQ ID NO:7) (B), VWCRADKRC (SEQ ID NO:6) (C) and THSDARRRE (SEQ ID NO:19) and the control peptides (D). Strikingly, all three cyclic peptides but neither linear nor control peptides completely inhibited platelet aggregation at a concentration of 90 µM. In correlation with the integrin $\alpha_{IIb}\beta_3$/fibrinogen interaction assay, cyclic peptide VWCRADRRC (SEQ ID NO:5), the only peptide to inhibit platelet aggregation at a concentration as low as 9 µM (FIG. 5A), was again found to be the most potent inhibitor.

While their potential application as anti-thrombotic drugs overlaps with abciximab, the RAD antibodies we describe here have several distinctive features. First, they are human antibodies, which are less likely to induce an immune response in the patients. Second, like RGD peptides and peptidomimetics (Xiong, J. P., Stehle, T., Zhang, R., Joachimiak, A., Frech, M., Goodman, S. L., and Arnaout, M. A. (2002) Crystal structure of the extracellular segment of integrin alpha Vbeta3 in complex with an Arg-Gly-Asp ligand. Science 296, 151-155), the RAD antibodies directly block the RGD binding site of integrin $\alpha_{IIb}\beta_3$. By contrast, the mechanism of integrin $\alpha_{IIb}\beta_3$ ligation by abciximab, which does not contain an RGD or RGD-like motif, is thought to involve steric or allosteric hindrance rather than direct blocking of the RGD binding site. Third, the RAD antibodies selectively bind to integrin $\alpha_{IIb}\beta_3$, whereas abciximab does not differentiate between integrins $\alpha_v\beta_3$ and $\alpha_{IIb}\beta_3$. The cross-reactivity of abciximab is analogous to our earlier integrin binding synthetic antibodies (Barbas, C. F., 3rd, Languino, L. R., and Smith, J. W. (1993) High-affinity self-reactive human antibodies by design and selection: targeting the integrin ligand binding site. Proc Natl Acad Sci USA 90, 10003-10007; Smith, J. W., Hu, D., Satterthwait, A., Pinz-Sweeney, S., and Barbas, C. F., 3rd (1994) Building synthetic antibodies as adhesive ligands for integrins. J Biol Chem 269, 32788-32795).

Acute thrombocytopenia whose cause is not known is one of the principal safety issues with integrin $\alpha_{IIb}\beta_3$ inhibitors. As mentioned above, human antibodies against the mouse variable domains of abciximab were reported as the main cause of platelet destruction in patients who developed severe thrombocytopenia after being given abciximab a second time (Curtis, B. R., Swyers, J., Divgi, A., McFarland, J. G., and Aster, R. H. (2002) Thrombocytopenia after second exposure to abciximab is caused by antibodies that recognize abciximab-coated platelets. Blood 99, 2054-2059). This finding might necessitate a further humanization of abciximab by grafting its CDRs onto the framework of human variable domains (Rader, C., Ritter, G., Nathan, S., Elia, M., Gout, I., Jungbluth, A. A., Cohen, L. S., Welt, S., Old, L. J., and Barbas, C. F., 3rd (2000) The rabbit antibody repertoire as a novel source for the generation of therapeutic human antibodies. J Biol Chem 275, 13668-13676). However, if not accompanied by framework fine tuning based on detailed structural information of the antibody, this CDR grafting strategy often yields antibodies with greatly reduced affinity to the antigen as in the case of anti-integrin $\alpha_{IIb}\beta_3$ monoclonal antibody YM337, which is currently evaluated in clinical trials (Suzuki, K., Sato, K., Kamohara, M., Kaku, S., Kawasaki, T., Yano, S., and Iizumi, Y. (2002) Comparative studies of a humanized anti-glycoprotein IIb/IIIa monoclonal antibody, YM337, and abciximab on in vitro antiplatelet effect and binding properties. Biol Pharm Bull 25, 1006-1012; Co, M. S., Yano, S., Hsu, R. K., Landolfi, N. F., Vasquez, M., Cole, M., Tso, J. T., Bringman, T., Laird, W., Hudson, D., and et al. (1994) A humanized antibody specific for the platelet integrin gpIIb/IIIa. J Immunol 152, 2968-2976). As the RAD antibodies are entirely composed of human sequences, except for the synthetic HCDR3, they are expected to be less immunogenic than chimeric or humanized antibodies. However, the induction of human anti-idiotypic antibodies by our RAD antibodies is possible. Since circulating anti-idiotypic antibodies would compete with platelet integrin $\alpha_{IIb}\beta_3$ for RAD antibody binding rather than bind to the platelet surface through the RAD antibodies, it is a reasonable assumption that they would not cause severe thrombocytopenia. An interesting recent finding was that human antibodies that selectively recognized integrin $\alpha_{IIb}\beta_3$ when complexed with tirofiban and eptifibatide were found in the very limited number of patients who developed severe thrombocytopenia after being treated with the small molecule drugs (Bougie, D. W., Wilker, P. R., Wuitschick, E. D., Curtis, B. R., Malik, M., Levine, S., Lind, R. N., Pereira, J., and Aster, R. H. (2002) Acute thrombocytopenia after treatment with tirofiban or eptifibatide is associated with antibodies specific for ligand-occupied GPIIb/IIIa. Blood 100, 2071-2076). In this context, the possibility remains that RAD antibodies could cause thrombocytopenia by inducing the display of immunogenic epitopes on integrin $\alpha_{IIb}\beta_3$ as their binding mode mimics the small molecule drugs.

Several mouse monoclonal antibodies (mAbs) specific for integrin $\alpha_{IIb}\beta_3$, including LJ-CP3, OPG2, and PAC-1 (Puzon-McLaughlin, W., Kamata, T., and Takada, Y. (2000) Multiple discontinuous ligand-mimetic antibody binding sites define a ligand binding pocket in integrin alpha(IIb)beta(3). J Biol Chem 275, 7795-7802; Kamata, T., Irie, A., Tokuhira, M., and Takada, Y. (1996) Critical residues of integrin alphaIIb subunit for binding of alphaIIbbeta3 (glycoprotein IIb-IIIa) to fibrinogen and ligand-mimetic antibodies (PAC-1, OP-G2, and LJ-CP3). J Biol Chem 271, 18610-18615; Prammer, K. V., Boyer, J., Ugen, K., Shattil, S. J., and Kieber-Emmons, T. (1994) Bioactive Arg-Gly-Asp conformations in anti-integrin GPIIb-IIIa antibodies. Receptor 4, 93-108; Tomiyama, Y., Brojer, E., Ruggeri, Z. M., Shattil, S. J., Smiltneck, J., Gorski, J., Kumar, A., Kieber-Emmons, T., and Kunicki, T. J. (1992) A molecular model of RGD ligands. Antibody D gene segments that direct specificity for the integrin alpha IIb beta 3. J Biol Chem 267, 18085-18092; Niiya, K., Hodson, E., Bader, R., Byers-Ward, V., Koziol, J. A., Plow, E. F., and Ruggeri, Z. M. (1987) Increased surface expression of the membrane glycoprotein IIb/IIIa complex induced by platelet activation. Relationship to the binding of fibrinogen and platelet aggregation. Blood 70, 475-483; Bennett, J. S., Hoxie, J. A., Leitman, S. F., Vilaire, G., and Cines, D. B. (1983) Inhibition of fibrinogen binding to stimulated human platelets by a monoclonal antibody. Proc Natl Acad Sci USA 80, 2417-2421) contain an RYD motif in HCDR3. The binding of these mouse mAbs to integrin $\alpha_{IIb}\beta_3$ could be completely blocked by RGD peptides, suggesting that their RYD motif mediates a direct interaction with the RGD binding site. Interestingly, mouse mAb, 16N7C2, which contains an RGD motif in HCDR3, did not differentiate between the $\beta_3$ integrins (Deckmyn, H., Stanssens, P., Hoet, B., Declerck, P. J., Lauwereys, M., Gansemans, Y., Tornai, I., and Vermylen, J. (1994) An echistatin-like Arg-Gly-Asp (RGD)-containing sequence in the heavy chain CDR3 of a murine monoclonal antibody that inhibits human platelet glycoprotein IIb/IIIa function. Br J Haematol 87, 562-571). Thus, similar to our synthetic RAD motif, the native RYD motif in some contexts provide for selective recognition of integrin $\alpha_{IIb}\beta_3$. However, in contrast to the synthetic RAD antibodies, neither LJ-CP3, OPG2, or PAC-1 contain a disulfide bridge in HCDR3 that displays the RGD-like motif (Tomiyama, Y., Brojer, E., Ruggeri, Z. M., Shattil, S. J., Smiltneck, J., Gorski, J., Kumar, A., Kieber-Emmons, T., and Kunicki, T. J. (1992) A molecular model of RGD ligands. Antibody D gene segments that direct specificity for the integrin alpha IIb beta 3. *J Biol Chem* 267, 18085-18092) suggesting either a limitation in the structural diversity that can be achieved by VDJ recombination or a selection against disulfide bridges in HCDR3. Previously, we selected human antibodies with a synthetically grafted RGD motif or RGD-mimicking motif in HCDR3 for binding to integrins $\alpha_v\beta_3$ and $\alpha_{IIb}\beta_3$ (Barbas, C. F., 3rd, Languino, L. R., and Smith, J. W. (1993) High-affinity self-reactive human antibodies by design and selection: targeting the integrin ligand binding site. *Proc Natl Acad Sci USA* 90, 10003-10007; Smith, J. W., Hu, D., Satterthwait, A., Pinz-Sweeney, S., and Barbas, C. F., 3rd (1994) Building synthetic antibodies as adhesive ligands for integrins. *J Biol Chem* 269, 32788-32795; Barbas, C. F., 3rd (1993) Recent advances in phage display. *Curr Opin Biotechnol* 4, 526-530). None of the selected antibodies were exclusively specific for either integrin. In an attempt to select antibodies with higher specificity, we generated a new synthetic human antibody library with the randomized HCDR3 sequence VGXXXRADXXXYAMDV (SEQ ID NO:3). In addition to replacing the RGD-motif by an RAD motif, an important distinction of the new library was the removal of a $CX_9C$ disulfide bridge that embraced the integrin binding motif and its flanking residues in previous libraries. Interestingly, the selection of the new library against integrin $\alpha_{IIb}\beta_3$ yielded a new motif-displaying disulfide bridge of the type $CX_5C$ that was found in 90% of the selected antibody sequences. This smaller loop structure, whose selection within the previous $CX_9C$ disulfide bridge would have been very unlikely, if not impossible, resulted in an exceptional selectivity toward integrin $\alpha_{IIb}\beta_3$.

The structural constraints of the selected XXXRADXXX (SEQ ID NO:22) motifs within HCDR3 prompted us to dissect them from the antibody scaffold and evaluate their functional properties. Three synthetic peptides that display the RAD motif within a $CX_5C$ disulfide bridge, VWCRADRRC (SEQ ID NO:5), VWCRADKRC (SEQ ID NO:6), and VVCRADRRC (SEQ ID NO:7), but not the linear synthetic peptide THSRADRRE (SEQ ID NO:19), inhibited the binding of the selected RAD antibodies to integrin $\alpha_{IIb}\beta_3$, the binding of fibrinogen to integrin $\alpha_{IIb}\beta_3$, as well as platelet aggregation. Peptide antagonists for integrin $\alpha_{IIb}\beta_3$ have been selected from peptide libraries by phage display (O'Neil, K. T., Hoess, R. H., Jackson, S. A., Ramachandran, N. S., Mousa, S. A., and DeGrado, W. F. (1992) Identification of novel peptide antagonists for GPIIb/IIIa from a conformationally constrained phage peptide library. *Proteins* 14, 509-515; Koivunen, E., Wang, B., and Ruoslahti, E. (1995) Phage libraries displaying cyclic peptides with different ring sizes: ligand specificities of the RGD-directed integrins. *Biotechnology* (N Y) 13, 265-270; Koivunen, E., Restel, B. H., Rajotte, D., Landenranta, J., Hagedorn, M., Arap, W., and Pasqualini, R. (1999) Integrin-binding peptides derived from phage display libraries. *Methods Mol Biol* 129, 3-17). Constrained peptide libraries of the type $CX_5C$, $CX_6C$, $CX_7C$, and $CX_9$ were used. However, only the $CX_6C$ and $CX_7C$ peptide libraries yielded binders to integrin $\alpha_{IIb}\beta_3$. The selected sequences could be categorized into two groups, those containing an RGD motif and those containing an RGD-like motif, in which either the glycine or arginine residue of RGD was replaced. The central glycine was substituted by a variety of different amino acid residues such as serine, threonine, leucine, alanine, glutamine, histidine, and methionine. Two peptides; CRADVPLC (SEQ ID NO:23) and CMSRADRPC (SEQ ID NO:24) contained an RAD motif. The RGD-containing sequences selected on integrin $\alpha_{IIb}\beta_3$ differed from those selected on integrin $\alpha_v\beta_3$ and $\alpha_5\beta_1$ in that aromatic residues Trp, Phe, or Tyr were enriched at the position immediately C-terminal to the RGD motif. In addition, several sequences contained one or two basic residues outside the RGD motif. However, none of the selected peptide sequences shared similarity with our selected HCDR3 sequences VWCRADKRC (SEQ ID NO:6), VWCRADRRC (SEQ ID NO:5), and VVCRADRRC (SEQ ID NO:7). Of note is the fact that the $CX_5C$ peptide library, which includes our $CX_5C$ core consensus sequence CRAD(K/R)RC, did not yield any binding peptide to integrin $\alpha_{IIb}\beta_3$, suggesting that the N-terminal VW or VV residues in our selected HCDR3 sequences play an essential role in the interaction with integrin $\alpha_{IIb}\beta_3$.

Phage display of both peptide and antibody libraries has become a standard technology for a variety of applications in research and development (Barbas, C. F., 3rd, Burton, D. R., Scott, J. K., and Silverman, G. J. (2001) *Phage Display: A Laboratory Manual*, Cold Spring Harbor Laboratory Press, Cold Spring Harbor, N.Y.; B. K., Kasanov, J., and Yamabhai, M. (2001) Screening phage-displayed combinatorial peptide libraries. *Methods* 24, 240-246; Sidhu, S. S. (2000) Phage display in pharmaceutical biotechnology. *Curr Opin Biotechnol* 11, 610-616). The display of peptide libraries within the antibody immunoglobulin variable domain merges these technologies, providing an intriguing link between antibody, peptide, and peptidomimetic drug discovery. Here we demonstrated the efficacy of this approach to generate novel specific anti-receptor peptides and antibodies. The placement of bioactive and or binding peptides within an antibody scaffold or their generation within the scaffold provides for the rapid development of immunological agents that can be used as biological tools or therapeutics (Barbas, C. F., 3rd (1993) Recent advances in phage display. *Curr Opin Biotechnol* 4, 526-530). Often peptides themselves have compromised activity in vivo and their binding may be difficult to monitor, however, their display within the context of an antibody addresses detection problems as well as problems associated with proteolysis of peptides and their rapid clearance since antibodies and antibody fragments exhibit relatively predictable pharmacokinetic behavior. Where it is desirable, for example in a cancer setting, the Fc region of the antibody can bestow cell-killing properties onto the peptide sequence as a result of immune effector coupling. We believe that this approach can be applied to a wide range of peptides with binding activity to rapidly generate useful immunological reagents (Brown, K. C. (2000) New approaches for cell-specific targeting: identification of cell-selective peptides from combinatorial libraries. *Curr Opin Chem Biol* 4, 16-21).

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

TABLE 1

HCDR3 sequences from synthetic human antibody libraries selected against β₃ integrins

| | | SEQ ID NO |
|---|---|---|
| Anti-gp120 Fab | VGP YSW DDS P-DQ NYYMDV | 53 |
| Fab library[a] | VGC XXX RGD XXX-CYYMDV | 54 |
| Fab-4 | --- TGQ --- WRS ----- | 55 |
| Fab-7 | --- TYG --- TRN ----- | 56 |
| Fab-8 | --- PIP --- WRE ----- | 57 |
| Fab-9 | --- SFG --- IRN ----- | 58 |
| Fab-10 | --- TWG --- ERN ----- | 59 |
| Fab-9 | VGC SFG RGD IRN-CYYMDV | 58 |
| MTF library[b] | VGC SFG XXX XRN-CYYMDV | 60 |
| MTF-2 | --- --- RTD Q-I ----- | 61 |
| MTF-10 | --- --- KGD N-I ----- | 62 |
| MTF-32 | --- --- RRD E-- ----- | 63 |
| MTF-40 | --- --- RND S-- ----- | 64 |
| MTF-1 | --- --- RVD D-- ----- | 65 |
| MTF-12 | --- --- RAD R-- ----- | 66 |
| MTF-15 | --- --- RSV D-- ----- | 67 |
| MTF-7 | --- --- KRD M-- ----- | 68 |
| MTF-13 | --- --- RWD A-- ----- | 69 |
| MTF-14 | --- --- RQD V-- ----- | 70 |
| MTF-20 | --- --- RDD G-- ----- | 71 |
| RAD library | VR XXX RAD XXX YAMDV | 72 |

[a]Iliarbas et al.(18); [b]Smith et al.(19)

TABLE 2

Sequences of RAD library Fabs selected against integrin α$_{IIb}$β$_3$

| Fab | VH | HCDR3 | VL | | SEQ ID NO |
|---|---|---|---|---|---|
| RAD1 | VH3 DP-47 | VR<u>THS</u>RAD<u>RRE</u>ANDV | VKIII | DPK22/A27 | 73 |
| RAD3 | VH3 DP-47 | VR<u>VVC</u>RAD<u>RRC</u>YAMDV | VKVI | DPK26/A26 | 74 |
| RAD4 | VH3 DP-47 | VG<u>VWC</u>RAD<u>RRC</u>YAMDV | VKVI | DPK26/A26 | 75 |
| RAD9 | VH3 DP-47 | VR<u>VVC</u>RAD<u>RRC</u>YAMDV | VKIII | Vg/38K | 74 |
| RAD11 | VH3 DP-47 | VG<u>VWC</u>RAD<u>RRC</u>YAMDV | VkVI | DPK26/A26 | 75 |
| RAD12 | VH3 DP-47 | VR<u>VVC</u>RAD<u>RRC</u>YAMDV | VL8 | 8a.88E1/DPL21 | 74 |
| RAD32 | VH3 DP-47 | VG<u>VWC</u>RAD<u>KRC</u>YAMDV | VKIII | 3A9 | 76 |
| RAD34 | VH3 DP-47 | VR<u>VVC</u>RAD<u>RRC</u>YAMDV | VL3 | V2-14 | 74 |
| RAD87 | VH3 DP-47 | VG<u>VVC</u>RAD<u>RRC</u>YAMDV | VL2 | 2c.118D9/v1-2 | 77 |
| RAD88 | VH3 DP-47 | VR<u>VWC</u>RAD<u>KRC</u>YAMDV | VKVI | DPK26/A26 | 78 |

TABLE 3

Comparison of Fab RAD87 and Fab abciximab

| Fab | K$_d$[a] | IC$_{50}$[b] | EC$_{50}$[c] |
|---|---|---|---|
| RAD87 | $3.3 \times 10^{-9}$ M | $8.0 \times 10^{-8}$ M | 60 nM |
| Abciximab | $1.1 \times 10^{-9}$ M | $9.0 \times 10^{-8}$ M | 45 nM |

[a]Dissociation constant for human integrin α$_{IIb}$β$_3$ binding.
[b]Required concentration for 50% inhibition in an interaction assay of human fibrinogen and human integrin α$_{IIb}$β$_3$.
[c]Required concentration for 50% inhibition in a human platelet aggregation assay.

What is claimed is:

1. An antibody that binds integrin $\alpha_{IIb}\beta_3$ and comprises a heavy chain variable region sequence selected from the group consisting of SEQ ID Nos:32, 33, 37 and 38.

2. The antibody of claim 1, wherein the antibody has a dissociation constant ($K_d$) from between $10^{-8}$ M and $10^{-11}$ M.

3. The antibody of claim 1 that is a human antibody.

4. A pharmaceutical composition comprising the antibody of claim 1 and a suitable pharmaceutical carrier in a form suitable for administration intravenously, intra-arterially, into the lymphatic circulation, intraperitoneally, transdermally, subcutaneously, intramuscularly, into the joint space, or by pulmonary administration.

5. An antibody as claimed in claim 1 for use as a medicament for treatment to prevent thrombosis in conditions selected from the group consisting of pulmonary embolism, transient ischemic attacks (TIAs), deep vein thrombosis, coronary bypass surgery, and surgery to insert a prosthetic valve or vessel in autologous, non-autologous or synthetic vessel graft.

6. An antibody as claimed in claim 1 for use as a medicament for treatment to prevent thrombosis in procedure selected from the group consisting of angioplasty procedures performed by balloon, coronary atherectomy, and laser angioplasty.

7. A method of inhibiting platelet aggregation comprising contacting platelets with an effective inhibitory amount of the antibody of claim 1.

8. A method of inhibiting binding of fibrinogen to platelets comprising contacting platelets with an effective inhibitory amount of the antibody of claim 1.

9. A method of treating a subject to treat a disorder of thrombus formation, the disorder selected from the group consisting of thrombosis in pulmonary embolism, transient ischemic attacks (TIAs), deep vein thrombosis, coronary bypass surgery, surgery to insert a prosthetic valve or vessel in autologous, non-autologous, or synthetic vessel graft the method comprising administering to the subject an amount of an antibody as claimed in claim 1 effective to achieve the desired treatment.

10. A method of treating a subject to treat a disorder of thrombus formation, the disorder selected from the group consisting of thrombosis in pulmonary embolism, transient ischemic attacks (TIAs), deep vein thrombosis, coronary bypass surgery, surgery to insert a prosthetic valve or vessel in autologous, non-autologous, or synthetic vessel graft, the method comprising administering to the subject an amount of a pharmaceutical composition as claimed in claim 4 effective to achieve the desired treatment.

* * * * *